US012233312B2

United States Patent
Min et al.

(10) Patent No.: US 12,233,312 B2
(45) Date of Patent: Feb. 25, 2025

(54) WEARABLE DEVICE, METHOD, AND NON-TRANSITORY COMPUTER READABLE STORAGE MEDIUM INCLUDING BODY TEMPERATURE SENSOR

(71) Applicant: SAMSUNG ELECTRONICS CO., LTD., Suwon-si (KR)

(72) Inventors: Eungi Min, Suwon-si (KR); Jeongmin Park, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 227 days.

(21) Appl. No.: 17/898,032

(22) Filed: Aug. 29, 2022

(65) Prior Publication Data
US 2023/0149775 A1    May 18, 2023

Related U.S. Application Data

(63) Continuation of application No. PCT/KR2022/011924, filed on Aug. 10, 2022.

(30) Foreign Application Priority Data

Nov. 14, 2021  (KR) .......................... 10-2021-0156217
Dec. 27, 2021  (KR) .......................... 10-2021-0188340

(51) Int. Cl.
A63B 24/00      (2006.01)
G04G 21/02      (2010.01)

(52) U.S. Cl.
CPC ....... *A63B 24/0062* (2013.01); *G04G 21/025* (2013.01); *A63B 2220/72* (2013.01);
(Continued)

(58) Field of Classification Search
CPC ............ A63B 24/0062; A63B 2220/72; A63B 2220/75; A63B 2220/836; A63B 2230/06;
(Continued)

(56) References Cited

U.S. PATENT DOCUMENTS 7,867,142 B2    1/2011  Kim et al.
9,682,306 B2    6/2017  Lin et al.
(Continued)

FOREIGN PATENT DOCUMENTS

JP    H06142087 A    5/1994
KR    100714093 B1   5/2007
(Continued)

OTHER PUBLICATIONS

International Search Report and Written Opinion for International Application No. PCT/KR2022/011924; International Filing Date Aug. 10, 2022; Date of Mailing Nov. 21, 2022; 13 Pages.
(Continued)

*Primary Examiner* — Masud Ahmed
(74) *Attorney, Agent, or Firm* — CANTOR COLBURN LLP

(57) ABSTRACT

A wearable device includes at least one memory, at least one sensor, a display, and at least one processor configured to receive, via the display, an input with respect to an item among a plurality of items respectively representing an exercise plan; in response to receiving the input, acquire, via the sensor, information for a first body temperature of a user wearing the wearable device; in response to identifying that the first body temperature is less than a first reference temperature, display a second screen guiding a warm-up exercise distinguishable from a first screen guiding the exercise plan indicated by the item corresponding to the input; acquire, via the sensor, a second body temperature of the user, while the second screen is displayed; and in response to identifying that the second body temperature reaches a second reference temperature, switch the second screen to the first screen.

20 Claims, 23 Drawing Sheets

(52) U.S. Cl.
CPC ..... *A63B 2220/75* (2013.01); *A63B 2220/836* (2013.01); *A63B 2230/06* (2013.01); *A63B 2230/50* (2013.01)

(58) Field of Classification Search
CPC .. A63B 2230/50; A63B 24/00; G04G 21/025; G04G 9/0064; G04G 9/007; G04G 21/04; G04G 21/00; A61B 5/00; A61B 5/0205; A61B 5/11; G16H 20/30
See application file for complete search history.

(56) References Cited

U.S. PATENT DOCUMENTS

| | | | |
|---|---|---|---|
| 11,875,890 B2* | 1/2024 | Worrell | G06Q 30/0282 |
| 2007/0027000 A1* | 2/2007 | Shirai | A63B 71/0686 |
| | | | 482/8 |
| 2007/0049461 A1* | 3/2007 | Kim | G16H 40/63 |
| | | | 482/8 |
| 2015/0066526 A1 | 3/2015 | Cheng et al. | |
| 2016/0151668 A1 | 6/2016 | Barnes et al. | |
| 2017/0128024 A1 | 5/2017 | Gelissen et al. | |
| 2017/0258367 A1* | 9/2017 | Cheng | A61B 5/0022 |
| 2019/0009136 A1* | 1/2019 | Lee | G16H 40/63 |

FOREIGN PATENT DOCUMENTS

| | | |
|---|---|---|
| KR | 101384299 B1 | 4/2014 |
| KR | 101687252 B1 | 12/2016 |
| KR | 20170095691 A | 8/2017 |
| KR | 20190119900 A | 10/2019 |
| KR | 102245338 B1 | 4/2021 |
| KR | 20210052658 A | 5/2021 |
| KR | 102297367 B1 | 9/2021 |
| WO | 2007061185 A1 | 5/2007 |

OTHER PUBLICATIONS

Extended European Search Report corresponding to Application No. 22892981.6-1113; Dated Nov. 12, 2024.

* cited by examiner

WEARABLE DEVICE, METHOD, AND NON-TRANSITORY COMPUTER READABLE STORAGE MEDIUM INCLUDING BODY TEMPERATURE SENSOR

CROSS-REFERENCE TO RELATED APPLICATION(S)

This application is a continuation application, claiming priority under § 365 (c), of an International application No. PCT/KR2022/011924, filed on Aug. 10, 2022, which is based on and claims the benefit of a Korean patent application number 10-2021-0156217, filed on Nov. 14, 2021, in the Korean Intellectual Property Office, and of a Korean patent application number 10-2021-0188340, filed on Dec. 27, 2021, in the Korean Intellectual Property Office, the disclosure of each of which is incorporated by reference herein in its entirety.

BACKGROUND

Technical Field

The following description relates to a wearable device, a method, and a non-transitory computer readable storage medium including a body temperature sensor.

Description of Related Art

As interest in health has recently increased, various electronic devices for measuring a user's health state have been proposed, and various services for the user's health state have also been provided. For example, a wearable device may guide a plurality of exercise plans to the user and obtain biometric data of the user.

A conventional wearable device did not guide a warm-up exercise or cool-down exercise before guiding a plurality of exercise plans, and even when the conventional wearable device guides the warm-up exercise or the cool-down exercise, it only guides the warm-up exercise or the cool-down exercise of a fixed plan, and does not provide a guide in consideration of a user's current state (e.g., body temperature and heart rate). Accordingly, a method for guiding the warm-up exercise or the cool-down exercise based on the user's current state is required.

SUMMARY

The conventional wearable device did not guide the warm-up exercise before performing the main exercise or provide an appropriate cool-down exercise after the main exercise was completed. In addition, the conventional wearable device is limited to a one-sided method of providing a guide for a pre-stored stretching posture and number of times without considering the current state of the user.

Accordingly, a method for measuring the user's current state and providing the warm-up exercise or the cool-down exercise in consideration of the measured user's current state is required.

The technical problems to be achieved in this document are not limited to those described above, and other technical problems not mentioned herein will be clearly understood by those having ordinary knowledge in the art to which the present disclosure belongs, from the following description.

According to an embodiment, a wearable device may include at least one memory configured to store instructions, at least one processor, at least one sensor, and a display. The at least one processor, when the instructions are executed, is configured to receive, via the display, an input with respect to an item among a plurality of items respectively representing an exercise plan; in response to the receiving of the input. The at least one processor, when the instructions are executed, is configured to obtain, via the at least one sensor, an information for a first body temperature of a user wearing the wearable device. The at least one processor, when the instructions are executed, is configured to display a second screen guiding a warm-up exercise distinguishable from a first screen guiding the exercise plan indicated by the item corresponding to the input in response to identifying that the first body temperature is less than a first reference temperature. The at least one processor, when the instructions are executed, is configured to obtain, via the at least one sensor, a second body temperature of the user, while the second screen is displayed. The at least one processor, when the instructions are executed, is configured to switch the second screen to the first screen in response to identifying that the second body temperature reaches to a second reference temperature.

According to an embodiment, a wearable device may include at least one memory configured to store instructions, at least one processor, at least one sensor, and a display. The at least one processor, when the instructions are executed, is configured to receive an input requesting an end of an exercise plan displayed via the display; in response to receiving of the input. The at least one processor, when the instructions are executed, is configured to obtain, via the at least one sensor, information for a first body temperature of a user wearing the wearable device. The at least one processor, when the instructions are executed, is configured to display a second screen guiding a cool-down exercise distinguishable from a first screen displayed responsive to the end of the exercise plan in response to identifying that the first body temperature exceeds a first reference temperature. The at least one processor, when the instructions are executed, is configured to obtain, via the at least one sensor, a second body temperature of the user, while the second screen is displayed. The at least one processor, when the instructions are executed, is configured to switch the second screen to the first screen in response to identifying that the second body temperature reaches to a second reference temperature lower than the first reference temperature.

The effects that can be obtained from the present disclosure are not limited to those described above, and any other effects not mentioned herein will be clearly understood by those having ordinary knowledge in the art to which the present disclosure belongs, from the following description.

DETAILED DESCRIPTION

According to an embodiment, the wearable device can reduce a risk of an injury of the user and increase an effect of recovering from fatigue after exercise by guiding the warm-up or cool-down exercise suitable for the user in consideration of biometric data (e.g., heart rate and/or body temperature).

Figure 1:
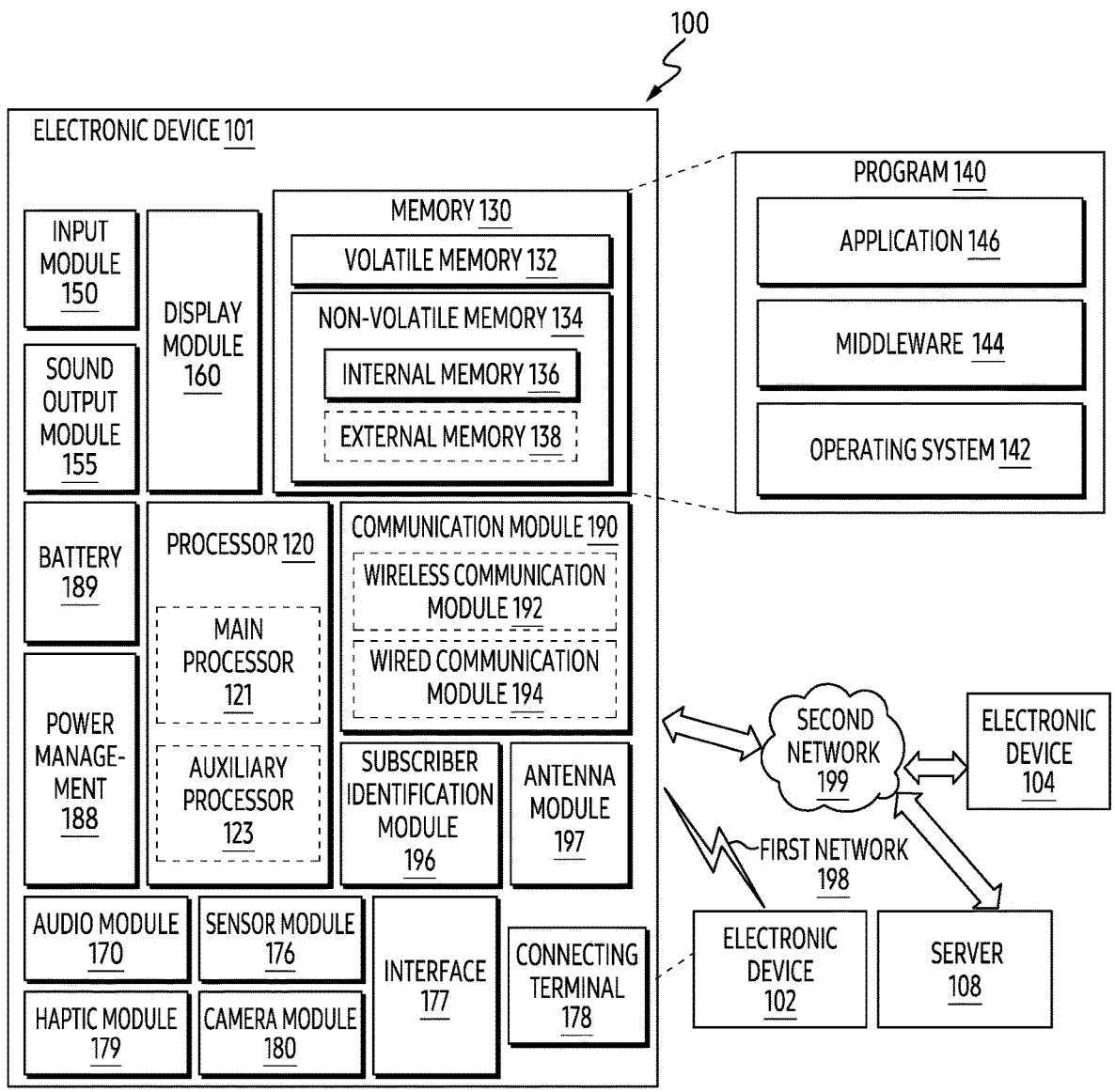
FIG. 1 is a block diagram of an electronic device in a network environment according to various embodiments.

FIG. 1 is a block diagram of an electronic device 101 in a network environment 100 according to various embodiments.

Referring to FIG. 1, in a network environment 100, an electronic device 101 may communicate with an electronic device 102 through a first network 198 (e.g., a local area wireless communication network) or communicate with at least one of an electronic device 104 or a server 108 through a second network 199 (e.g., a wide area wireless communication network). According to one embodiment, the electronic device 101 may communicate with the electronic device 104 through the server 108. According to one embodiment, the electronic device 101 may include a processor 120, a memory 130, an input module 150, a sound output module 155, a display module 160, an audio module 170, a sensor module 176, an interface 177, a connection terminal 178, a haptic module 179, a camera module 180, a power management module 188, a battery 189, a communication module 190, a subscriber identification module 196, or an antenna module 197. In some embodiments, at least one of these components (e.g., the connection terminal 178) may be omitted from to the electronic device 101 or one or more other components may be added thereto. In some embodiments, some of these components (e.g., the sensor module 176, the camera module 180, or the antenna module 197) may be integrated into one component (e.g., the display module 160).

The processor 120 may, for example, execute software (e.g., a program 140) to control at least one other component (e.g., hardware or software element) of the electronic device 101 connected to the processor 120 and perform various data processing or operation. According to one embodiment, as at least part of data processing or operation, the processor 120 may store instructions or data received from other components (e.g., the sensor module 176 or the communication module 190) into a volatile memory 132, process the instructions or data stored in the volatile memory 132, and store resulting data in a non-volatile memory 134. According to one embodiment, the processor 120 may include a main processor 121 (e.g., a central processing unit or an application processor) or an auxiliary processor 123 (e.g., a graphic processing unit, a neural processing unit (NPU), an image signal processor, a sensor hub processor, or a communication processor) being operable either independently of or in combination with the main processor 121. For example, when the electronic device 101 includes the main processor 121 and the auxiliary processor 123, the auxiliary processor 123 may be set to use less power than the main processor 121 or to be specialized for a certain function. The auxiliary processor 123 may be implemented separately from or as a part of the main processor 121.

The auxiliary processor 123 may, for example, control at least part of the functions or states related to at least one of the components of the electronic device 101 (e.g., the display module 160, the sensor module 176, or the communication module 190), on behalf of the main processor 121 while the main processor 121 is in an inactive state (e.g., a sleeping mode), or in combination with the main processor 121 while the main processor 121 is in an active state (e.g., an application execution mode). According to one embodiment, the auxiliary processor 123 (e.g., the image signal processor or the communication processor) may be implemented as a part of another component (e.g., the camera module 180 or the communication module 190) functionally related thereto. According to one embodiment, the auxiliary processor 123 (e.g., the neural processing unit) may include a hardware structure specialized for processing an artificial intelligence model. The artificial intelligence models may be created through machine learning. Such learning may be performed, for example, in the electronic device 101 itself on which the artificial intelligence model is performed, or may be performed through a separate server (e.g., the server 108). The learning algorithm may include, for example, supervised learning, unsupervised learning, semi-supervised learning, or reinforcement learning, but it is not limited to the above examples. The artificial intelligence model may include a plurality of artificial neural network layers. The artificial neural network may include one or more of a deep neural network (DNN), a convolutional neural network (CNN), a recurrent neural network (RNN), a restricted Boltzmann machine (RBM), a deep belief network (DBN), a bidirectional recurrent deep neural network (BRDNN), a deep Q-network or a combination of two or more thereof, but it is not limited to the above example. The artificial intelligence model may include a software structure, either in addition to the hardware structure or alternatively.

The memory 130 may store various data used by at least one component of the electronic device 101 (e.g., the processor 120 or the sensor module 176). The data may include, for example, software (e.g., the program 140) and input/output data for instructions related thereto. The memory 130 may include the volatile memory 132 or the non-volatile memory 134.

The program 140 may be stored as a software in the memory 130, and may include, for example, an operating system 142, a middleware 144, or at least one application 146.

The input module 150 may receive instructions or data to be used in a component (e.g., the processor 120) of the electronic device 101 from the outside (e.g., from a user) of the electronic device 101. The input module 150 may include, for example, a microphone, a mouse, a keyboard, a key (e.g., a button), or a digital pen (e.g., a stylus pen).

The sound output module 155 may output a sound signal to the outside of the electronic device 101. The sound output module 155 may include, for example, a speaker or a receiver. The speaker may be used for a general purpose such as playback or recording of multimedia. The receiver may be used to receive incoming calls. According to one embodiment, the receiver may be implemented separately from or as a part of the speaker.

The display module 160 may provide visual information to the outside of the electronic device 101 (e.g., a user). The display module 160 may include, for example, a display, a hologram apparatus or a projector, and a control circuit to control that device. According to one embodiment, the display module 160 may include a touch sensor configured to sense a touch, or a pressure sensor configured to measure intensity of a force generated by the touch.

The audio module 170 may convert a sound into an electric signal or, conversely, an electric signal into a sound. According to one embodiment, the audio module 170 may obtain a sound through the input module 150, or output a sound through the sound output module 155 or an external electronic device (e.g., the electronic device 101, a speaker or a headphone) connected directly or wirelessly with the electronic device 101.

The sensor module 176 may detect an operating state (such as e.g., power or temperature) of the electronic device 101, or an external environmental state (e.g., a user state), and generate an electrical signal or data value corresponding to the sensed state. According to one embodiment, the sensor module 176 may include, for example, a gesture sensor, a gyro sensor, a barometric pressure sensor, a magnetic sensor, an acceleration sensor, a grip sensor, a proximity sensor, a color sensor, an IR (infrared) sensor, a biometric sensor, a temperature sensor, a humidity sensor, or a luminance sensor.

The interface 177 may support one or more designated protocols that can be used for the electronic device 101 to directly or wirelessly connect with an external electronic device (e.g., the electronic device 102). According to one embodiment, the interface 177 may include, for example, a high definition multimedia interface (HDMI), a universal serial bus (USB) interface, an SD card interface, or an audio interface.

The connection terminal 178 may include a connector through which the electronic device 101 can be physically connected to an external electronic device (e.g., the electronic device 102). According to one embodiment, the connection terminal 178 may include, for example, an HDMI connector, a USB connector, an SD card connector, or an audio connector (e.g., a headphone connector).

The haptic module 179 may convert an electrical signal into either a mechanical stimulus (such as e.g., vibration or movement) or an electrical stimulus, which the user can perceive through tactile or kinesthetic sense. According to one embodiment, the haptic module 179 may include, for example, a motor, a piezoelectric element, or an electrical stimulation device.

The camera module 180 may capture still images and moving images. According to one embodiment, the camera module 180 may include one or more lenses, image sensors, image signal processors, or flashes.

The power management module 188 may be adapted to manage power supplied to the electronic device 101. According to one embodiment, the power management module 188 may be implemented as, for example, at least a part of a power management integrated circuit (PMIC).

The battery 189 may supply electrical power to at least one component of the electronic device 101. According to one embodiment, the battery 189 may include, for example, a non-rechargeable primary cell, a rechargeable secondary cell, or a fuel cell.

The communication module 190 may support to establish a direct (e.g., wired) communication channel or a wireless communication channel between the electronic device 101 and an external electronic device (e.g., the electronic device 102, the electronic device 104, or the server 108), and perform communications through the established communication channel. The communication module 190 may include one or more communication processors that can operate independently of the processor 120 (e.g., an application processor) and support direct (e.g., wired) communications or wireless communications. According to one embodiment, the communication module 190 may include a wireless communication module 192 (such as e.g., a cellular communication module, a short-range wireless communication module, or a global navigation satellite system (GNSS) communication module) or a wired communication module 194 (such as e.g., a local area network (LAN) communication module, or a power line communication module). A corresponding communication module of these communication modules may communicate with the external electronic device 104 via a first network 198 (e.g., a local area communication network such as e.g., Bluetooth, wireless fidelity (WiFi) direct, or infrared data association (IrDA)) or a second network 199 (e.g., a wide area communication network such as legacy cellular network, 5G network, next-generation communication network, Internet, or a computer network (e.g., LAN or WAN)). These various types of communication modules may be integrated into one component (e.g., a single chip) or may be implemented as a multiplicity of components (e.g., multiple chips) separate from each other. The wireless communication module 192 may use subscriber information (such as e.g., international mobile subscriber identifier (IMSI)) stored in the subscriber identification module 196 to identify or authenticate electronic device 101 within a communication network such as the first network 198 or the second network 199.

The wireless communication module 192 may support a 5G network after 4G network and a next-generation communication technology, for example, a new radio (NR) access technology. The NR access technology may support high-speed transmission of high-capacity data (i.e., eMBB: enhanced mobile broadband), minimization of terminal power and connectivity of massive terminals (mMTC: massive machine-type communications), or ultra-reliable & low-latency communications (URLLC). The wireless communication module 192 may support, for example, a high-frequency band (e.g., mmWave band) to achieve a high data rate. The wireless communication module 192 may support various technologies for securing better performance in the high-frequency band, such as for example, beamforming, massive multiple-input and multiple-output (massive MIMO), full-dimensional MIMO (FD-MIMO), array antenna, analog beam-forming, or large-scale antenna. The wireless communication module 192 may support various technical requirements prescribed by the electronic device 101, an external electronic device (e.g., the electronic device 104, or a network system (e.g., the second network 199). According to one embodiment, the wireless communication module 192 may support peak data rate (e.g., 20 Gbps or more) for realizing eMBB, loss coverage (e.g., 164 dB or less) for realizing mMTC, or U-plane latency for realizing URLLC (e.g., for each of downlink (DL) and uplink (UL), 0.5 ms or less, or round trip 1 ms or less) can be supported.

The antenna module 197 may transmit or receive a signal or power to/from the outside (e.g., an external electronic device). According to one embodiment, the antenna module 197 may include at least one antenna having a radiator a conductor or a conductive pattern formed on a substrate (e.g., a PCB). According to one embodiment, the antenna module 197 may include a plurality of antennas (e.g., an array antenna). In that case, at least one antenna suitable for a communication system used in a communication network such as e.g., the first network 198 or the second network 199 may be selected from the plurality of antennas by the communication module 190, for example. A signal or power may be transmitted or received between the communication module 190 and an external electronic device, via the at least one antenna selected. According to some embodiments, other devices or components, such as e.g., a radio frequency integrated circuit (RFIC), other than the radiator may be additionally formed as a part of the antenna module 197.

According to various embodiments, the antenna module 197 may form an mmWave antenna module. According to one embodiment, the mmWave antenna module may include a printed circuit board, an RFIC disposed on or adjacent to a first surface (e.g., bottom surface) of the printed circuit board and capable of supporting a designated high-frequency band (e.g., mmWave band), and a plurality of antennas (e.g., an array antenna) disposed on or adjacent to a second surface (e.g., top or side surface) of the printed circuit board and capable of transmitting or receiving signals in the designated high-frequency band.

At least some of the above components may be connected to each other through a certain communication scheme between peripheral devices (e.g., bus, general purpose input and output (GPIO), serial peripheral interface (SPI), mobile industry processor interface (MIPI), or the like) and may exchange signals (e.g., instructions or data) with each other.

According to one embodiment, instructions or data may be transmitted or received between the electronic device 101 and the external electronic device 104 via the server 108 connected to the second network 199. Each of the external electronic devices 102 or 104 may be the same as or different from the electronic device 101. According to one embodiment, all or part of the operations executed in the electronic device 101 may be executed in at least one of the external electronic devices 102 and 104, or the server 108. For example, when the electronic device 101 has to perform a certain function or service automatically or in response to a request from a user or another device, the electronic device 101 may request one or more external electronic devices to perform at least part of the function or service, instead of executing the function or service itself or in addition thereto. The one or more external electronic devices that have received the request may execute at least part of the requested function or service, or an additional function or service related to the request, and then transmit a result of the execution to the electronic device 101. The electronic device 101 may provide the result as it is or further process, so as to provide the same as at least part of a response to the request. For this purpose, it may be utilized, for example, cloud computing, distributed computing, mobile edge computing (MEC), or client-server computing technology. The electronic device 101 may provide an ultra-low latency service using, for example, distributed computing or mobile edge computing. In another embodiment, the external electronic device 104 may include an Internet of Things (IoT) device. The server 108 may be of an intelligent server using machine learning and/or neural networks. According to one embodiment, the external electronic device 104 or the server 108 may be incorporated into the second network 199. The electronic device 101 may be applied to an intelligent service (e.g., smart-home, smart-city, smart-car, or healthcare) based on 5G communication technology and IoT-related technology.

Figure 2A:
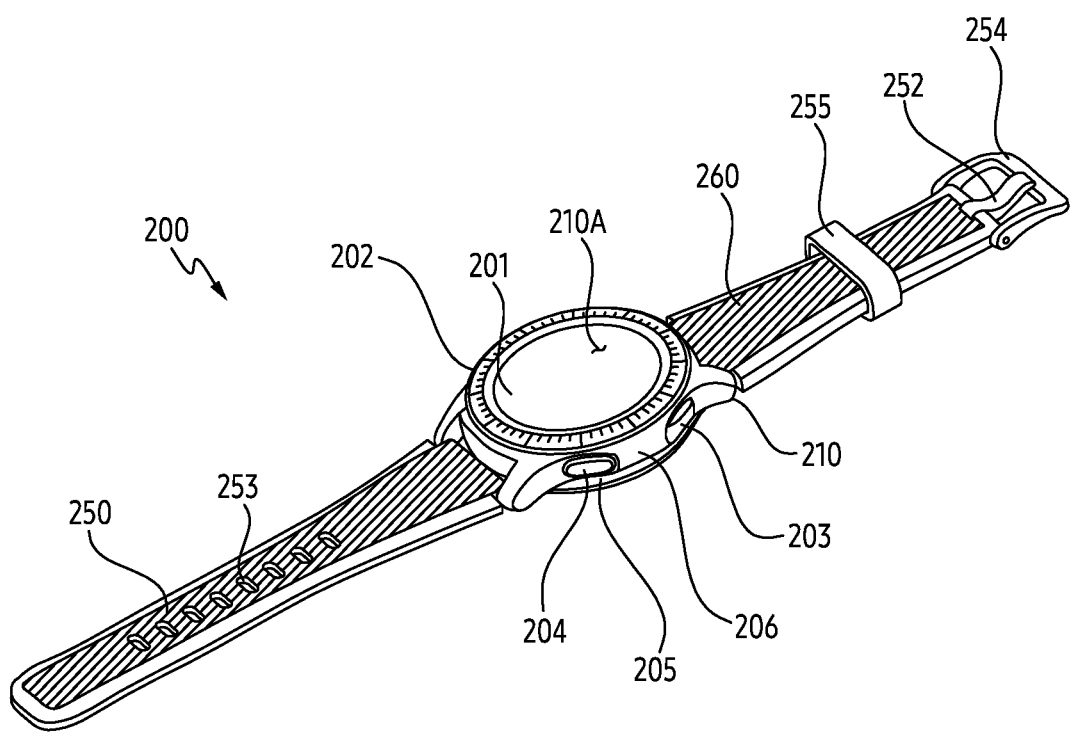
FIGS. 2A and 2B are perspective views of an electronic device according to an embodiment.
Figure 2B:
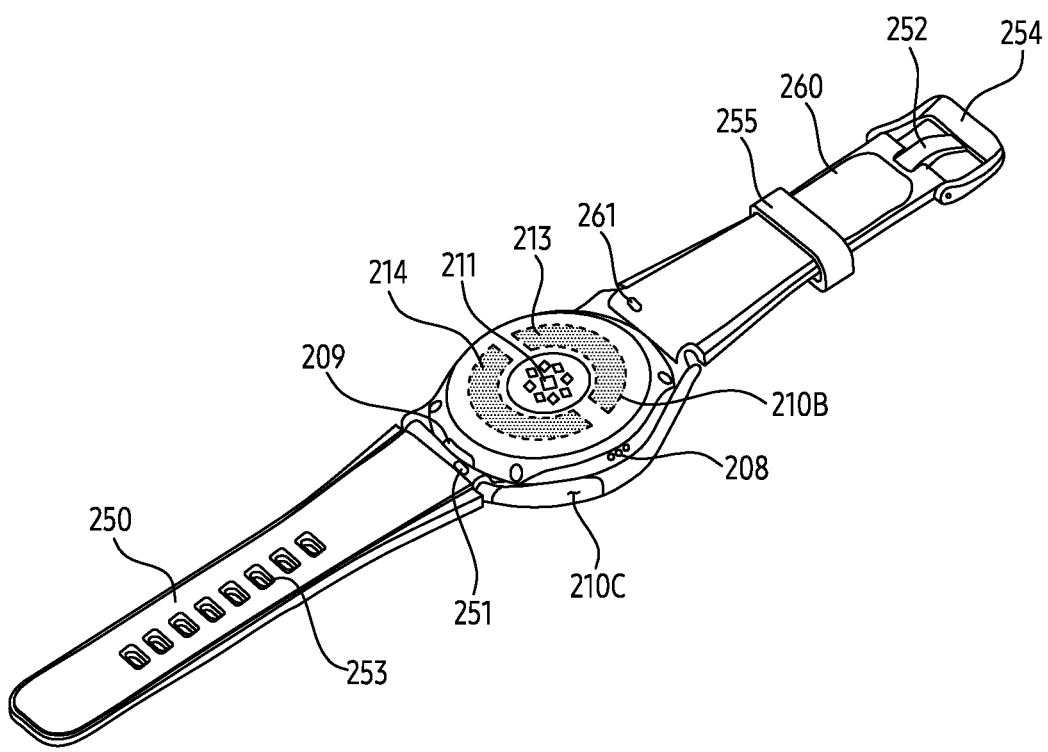

FIGS. 2A and 2B are perspective views of an electronic device according to an embodiment.

Referring to FIGS. 2A and 2B, an electronic device 200 (e.g., the electronic device 101 of FIG. 1) according to an embodiment may include a housing 210 including a first surface (or a front surface) 210A, a second surface (or a rear surface) 210B, and a side surface 210C surrounding a space between the first surface 210A and the second surface 210B and binding members 250 and 260 connected to at least a part of the housing 210 and configured to detachably attach the electronic device 200 to a part of the user's body (e.g., a wrist, an ankle, etc.). In another embodiment (not illustrated), the housing may also refer to a structure that forms a part of the first surface 210A, the second surface 210B, and the side surface 210C of FIG. 2A. According to an embodiment, at least a part of the first surface 210A may be formed by a substantially transparent front plate 201 (e.g., a glass plate or a polymer plate including various coating layers). The second surface 210B may be formed by a substantially opaque rear plate 207. The rear plate 207 may be formed by, for example, coated or colored glass, ceramic, polymer, metal (e.g., aluminum, stainless steel (STS), or magnesium), or a combination of at least two of the materials. The side surface 210C may be coupled to the front plate 201 and the rear plate 207, and may be formed by a side bezel structure (or "side member") 206 including a metal and/or a polymer. In some embodiments, the rear plate 207 and the side bezel structure 206 may be integrally formed and may include the same material (e.g., a metal material such as aluminum). The binding members 250 and 260 may be formed of various materials and shapes. An integral unit link and a plurality of unit links may be formed to flow with each other by a woven fabric, leather, rubber, urethane, metal, ceramic, or a combination of at least two of the materials.

According to an embodiment, the electronic device 200 may include at least one of a display 220 (see FIG. 3), an audio module 205 and 208, a sensor module 211, a key input device 202, 203 and 204, and a connector hole 209. In some embodiments, the electronic device 200 may omit at least one of the components (e.g., the key input devices 202, 203 and 204, the connector hole 209, or the sensor module 211) or may further include another component.

The display 220 may be exposed, for example, through a substantial portion of the front plate 201. A shape of the display 220 may be a shape corresponding to a shape of the front plate 20, and may have various shapes such as a circle, an oval, or a polygon. The display 220 may be coupled to or adjacent to a touch sensing circuit, a pressure sensor capable of measuring the strength (pressure) of a touch, and/or a fingerprint sensor.

The audio modules 205 and 208 may include a microphone hole 205 and a speaker hole 208. In the microphone hole 205, a microphone for obtaining an external sound may be disposed inside, and in some embodiments, a plurality of microphones may be disposed to detect the direction of the sound. The speaker hole 208 may be used as an external speaker and a receiver for calls. In some embodiments, the speaker hole 208 and the microphone hole 205 may be implemented as a single hole, or a speaker may be included without the speaker hole 208 (e.g., a piezo speaker).

The sensor module 211 may generate an electrical signal or data value corresponding to an internal operating state of the electronic device 200 or an external environmental state. The sensor module 211 may include, for example, a biometric sensor module 211 (e.g., an HRM sensor) disposed on the second surface 210B of the housing 210. The electronic device 200 may further include at least one of a sensor module not shown, for example, a gesture sensor, a gyro sensor, a pressure sensor, a magnetic sensor, an acceleration sensor, a grip sensor, a color sensor, an infrared sensor, a biometric sensor, a humidity sensor, and an illumination sensor.

The sensor module 211 may include electrode regions 213 and 214 forming a part of the surface of the electronic device 200 and a bio-signal detection circuit (not shown) electrically connected to the electrode regions 213 and 214. For example, the electrode regions 213 and 214 may include the first electrode region 213 and the second electrode region 214 disposed on the second surface 210B of the housing 210. The sensor module 211 may be configured such that the electrode regions 213 and 214 obtain an electrical signal from a part of the user's body, and a bio-signal detection circuit detects biometric information of the user based on the electrical signal.

The key input devices 202, 203, and 204 may include a wheel key 202 disposed on the first surface 210A of the housing 210 and rotatable in at least one direction, and/or side key buttons 203 and 204 disposed on the side surface 210C of the housing 210. The wheel key may have a shape corresponding to the shape of the front plate 201. In another embodiment, the electronic device 200 may not include some or all of the above-described key input devices 202, 203, and 204, and the not included key input devices 202, 203, and 204 may be implemented in other forms such as a soft key on the display 220. The connector hole 209 may accommodate connectors (e.g., USB connectors) for transmitting and receiving power and/or data to and from external electronic devices and may include another connector hole (not illustrated) capable of accommodating a connector for transmitting and receiving audio signals to and from an external electronic device. The electronic device 200 may further include, for example, a connector cover (not illustrated) that covers at least a part of the connector hole 209 and blocks the inflow of external foreign material into the connector hole.

The binding members 250 and 260 may be detachably attached to at least a part of the housing 210 using locking members 251, 261. The binding members 250 and 260 may include one or more of a fixing member 252, a fixing member fastening hole 253, a band guide member 254, and a band fixing ring 255.

The fixing member 252 may be configured to fix the housing 210 and the binding members 250 and 260 to a part of the user's body (e.g., a wrist, an ankle, etc.). The fixing member fastening hole 253 may fix the housing 210 and the binding members 250 and 260 to a part of the user's body corresponding to the fixing member 252. The band guide member 254 may be configured to limit a movement range of the fixing member 252 when the fixing member 252 is fastened to the fixing member fastening hole 253, so that the binding members 250 and 260 are attached in close contact with a part of the user's body. The band fixing ring 255 may limit the range of movement of the binding members 250 and 260 in a state in which the fixing member 252 and the fixing member fastening hole 253 are fastened.

Figure 3:
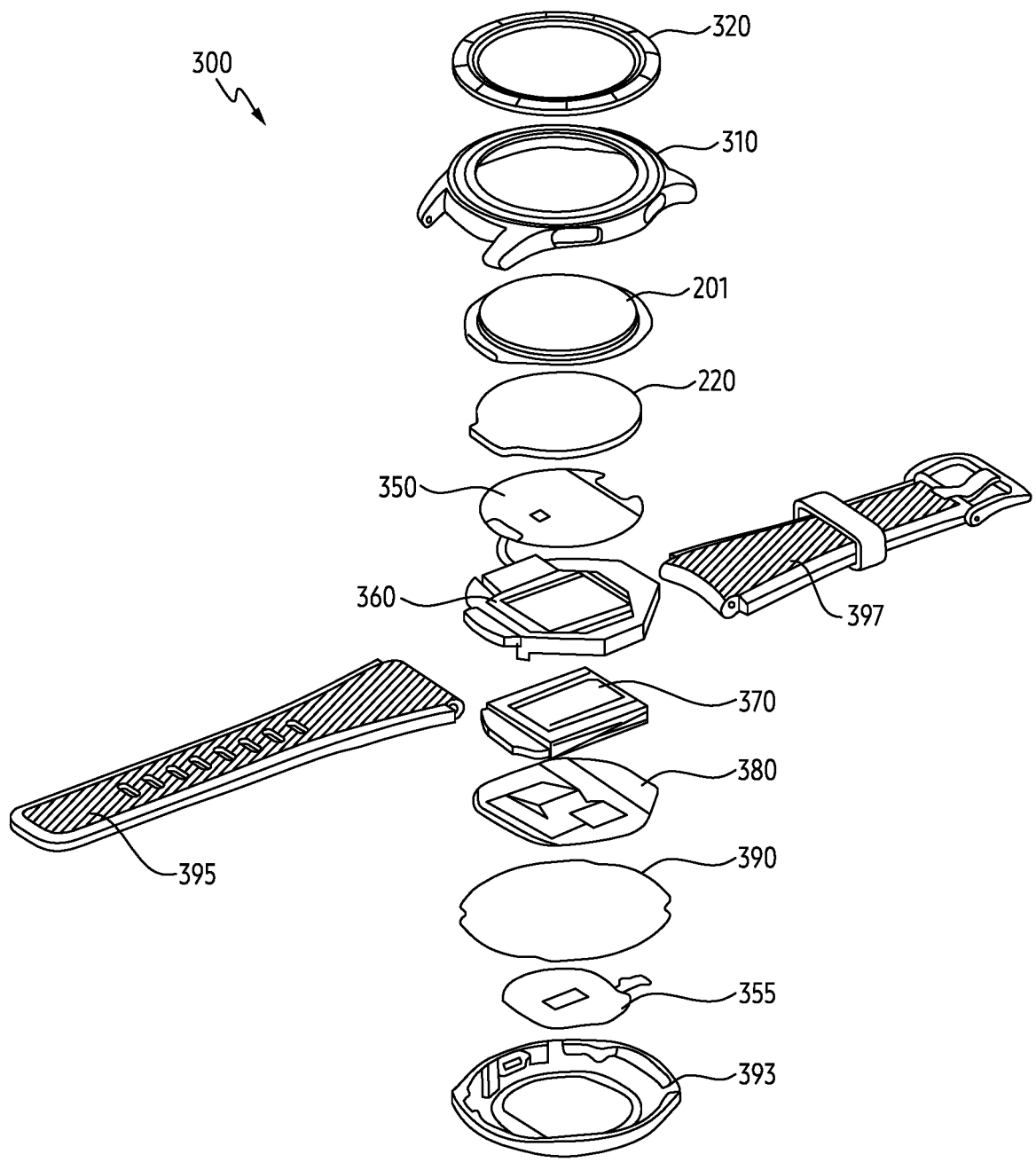
FIG. 3 is an exploded perspective view of an electronic device according to an embodiment.

FIG. 3 is an exploded perspective view of an electronic device according to an embodiment.

Referring to FIG. 3, an electronic device 300 (e.g., the electronic device 101 of FIG. 1, the electronic device 200 of FIG. 2A and/or FIG. 2B) may include a side bezel structure 310, a wheel key 320, a front plate 201, a display 220, a first antenna 350, a second antenna 355, a support member 360 (e.g., a bracket), a battery 370, a printed circuit board 380, a sealing member 390, and binding members 395 and 397. At least one of the components of the electronic device 300 may be the same as or similar to at least one of the components of the electronic device 200 of FIGS. 1, 2A, and/or 2B, and a repeated description thereof will be omitted. The support member 360 may be disposed inside the electronic device 300 to be connected to the side bezel structure 310 or may be integrally formed with the side bezel structure 310. The support member 360 may be formed of, for example, a metal material and/or a non-metal (e.g., a polymer) material. In the support member 360, the display 220 may be coupled to one surface and the printed circuit board 380 may be coupled to the other surface. A processor, a memory, and/or an interface may be mounted on the printed circuit board 380. The processor may include, for example, one or more of a central processing unit, an application processor, a graphic processing unit (GPU), an application processor sensor processor, or a communication processor.

The memory may include, for example, a volatile memory or a nonvolatile memory. The interface may include, for example, a high definition multimedia interface (HDMI), a universal serial bus (USB) interface, an SD card interface, and/or an audio interface. The interface may electrically or physically connect the electronic device 300 to an external electronic device, for example, and may include a USB connector, an SD card/MMC connector, or an audio connector.

The battery 370 is a device for supplying power to at least one component of the electronic device 300, and may include, for example, a non-rechargeable primary battery, a rechargeable secondary battery, or a fuel battery. At least a part of the battery 370 may be disposed on substantially the same plane as, for example, the printed circuit board 380. The battery 370 may be integrally disposed inside the electronic device 200 or may be detachably disposed from the electronic device 200.

The first antenna 350 may be disposed between the display 220 and the support member 360. The first antenna 350 may include, for example, a near field communication (NFC) antenna, a wireless charging antenna, and/or a magnetic secure transmission (MST) antenna. The first antenna 350 may, for example, perform short-range communication with an external device, wirelessly transmit and receive power required for charging, and transmit a short-range communication signal or a self-based signal including payment data. In another embodiment, an antenna structure may be formed by the side bezel structure 310 and/or a part of the support member 360 or a combination thereof.

The second antenna 355 may be disposed between the printed circuit board 380 and the rear plate 393. The second antenna 355 may include, for example, a near field communication (NFC) antenna, a wireless charging antenna, and/or a magnetic secure transmission (MST) antenna. For example, the second antenna 355 may perform short-range communication with an external device, wirelessly transmit and receive power required for charging, and may transmit a short-range communication signal or a self-based signal including payment data. In another embodiment, an antenna structure may be formed by the side bezel structure 310 and/or a part of the rear plate 393 or a combination thereof.

The sealing member 390 may be positioned between the side bezel structure 310 and the rear plate 393. The sealing member 390 may be configured to block moisture and foreign material flowing into a space surrounded by the side bezel structure 310 and the rear plate 393 from the outside.

Figure 4:
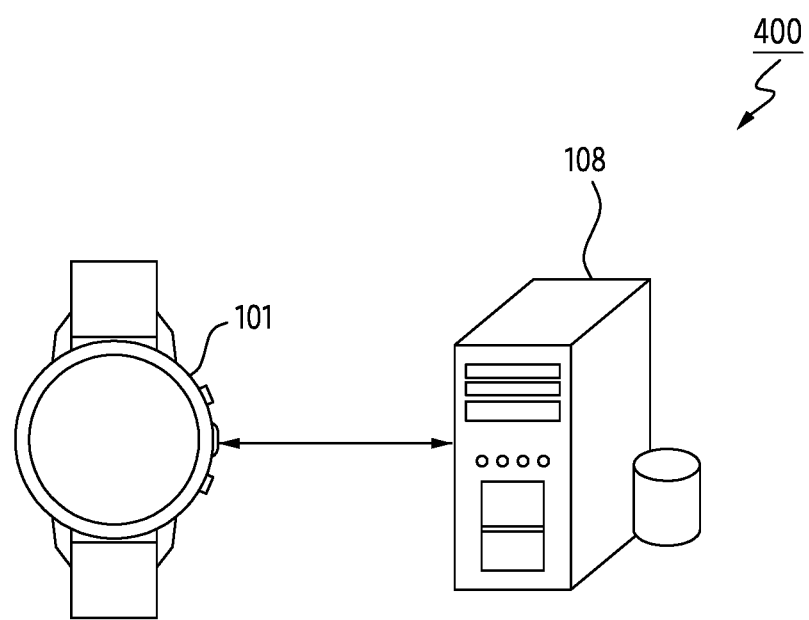
FIG. 4 illustrates an environment including an electronic device according to an embodiment.

FIG. 4 illustrates an environment 400 including an electronic device 101 according to an embodiment.

Referring to FIG. 4, the environment 400 may include an electronic device 101 and a server 108.

According to various embodiments, the electronic device 101 may operate by a user being worn. For example, the electronic device 101 may operate by being worn on a part of a user's body (e.g., a wrist). The electronic device 101 may have a watch shape.

According to an embodiment, the electronic device 101 may obtain a biometric data for a user by using a sensor module 211 (e.g., the sensor module 176 of FIG. 1). For example, the electronic device 101 may obtain an information on at least one of a heart rate, a body temperature, a blood pressure, an oxygen saturation, an electrocardiogram, a sleep status, a stress information, and a body composition.

According to an embodiment, the electronic device 101 may obtain a data on the movement (or displacement) of the user. For example, the electronic device 101 may obtain a user's movement based on at least one of an acceleration sensor (not shown), a gyro sensor (not shown), and a geomagnetic sensor (not shown) among the sensor module 211. For example, the electronic device 101 may identify whether the user is actually performing a guided exercise (e.g., warm-up exercise, cool-down exercise, and/or main exercise) via the display of the electronic device 101, based on the data on the user's movement.

According to various embodiments, the electronic device 101 may establish a connection with the server 108 by using the communication module 190 of FIG. 1. For example, the server 108 may store an information on a plurality of users including the user of the electronic device 101. For example, the electronic device 101 may receive an information for identifying a data on the user's physical condition from the server 108. The electronic device 101 may obtain a data on the user's physical condition based on the received information. For example, the data on the user's physical condition may include at least the user's height, weight, or body fat ratio. For another example, the electronic device 101 may transmit exercise record data to the server 108. The server 108 may store and/or manage exercise records for each of the plurality of users including the user of the electronic device 101. For example, the electronic device 101 may transmit exercise record data on the guided warm-up exercise to the server 108 before starting the main exercise.

In the above-described embodiment, the electronic device 101 is illustrated to establish a connection with the server 108 directly via the communication module 190, but is not limited thereto.

According to various embodiments, the electronic device 101 may establish a communication connection with an external electronic device (e.g., the electronic device 102 of FIG. 1). For example, the external electronic device (e.g., the electronic device 102 of FIG. 1) may be a user's smartphone. The communication module 190 may be a module for a Bluetooth connection or a module for Wi-Fi communication. The electronic device 101 may transmit data on the user's physical condition and/or exercise record data. The external electronic device 102 may transmit data on the physical condition and/or exercise record data received from the electronic device 101 via the communication connection to the server 108.

According to various embodiments, the electronic device 101 may establish a communication connection with an external wearable device (e.g., the electronic device 102 of FIG. 1). For example, the external wearable device may correspond to earbuds worn by the user. The electronic device 101 may use a sensing value obtained via the external wearable device. For example, the electronic device 101 may transmit a result of correcting the body temperature value sensed by the electronic device 101 to the server 108. The electronic device 101 may receive a value sensed by the user's ear temperature via the external wearable device. The electronic device 101 may correct the body temperature value sensed by the electronic device 101 based on the sensing value received from the external wearable device and transmit the corrected body temperature value to the server 108. For another example, when the user's ear temperature is determined to be the most reliable measurement of body temperature, The electronic device 101 may receive the temperature value sensed via the external wearable device and transmit the received temperature value to the server 108.

According to various embodiments, the electronic device 101 may establish a connection with an in-home device (e.g., a TV, a speaker, refrigerator, and/or a styler). For example, the electronic device 101 may establish a connection based on Bluetooth communication with the in-house device. When the user performs an exercise in the house, the electronic device 101 may perform a connection with the in-house device to transmit a body temperature value measured via the electronic device 101 to the in-house device. In this case, the transmission of the body temperature value may be based on connectionless communication based on an advertising packet, or may be based on transmission and reception via a data packet after establishing a Bluetooth session. The in-house device may provide information on a real-time body temperature change to the user by displaying the body temperature value received from the electronic device 101 via a screen or outputting it as a sound.

Figure 5A:
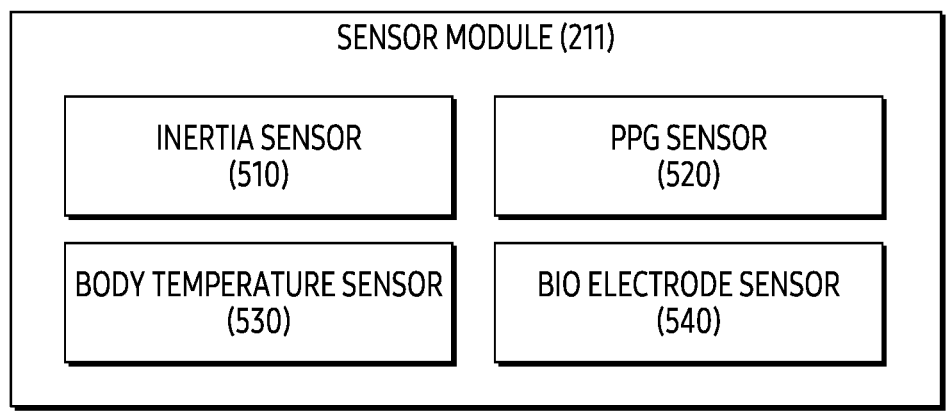
FIG. 5A is a block diagram of a sensor module according to various embodiments.
Figure 5B:
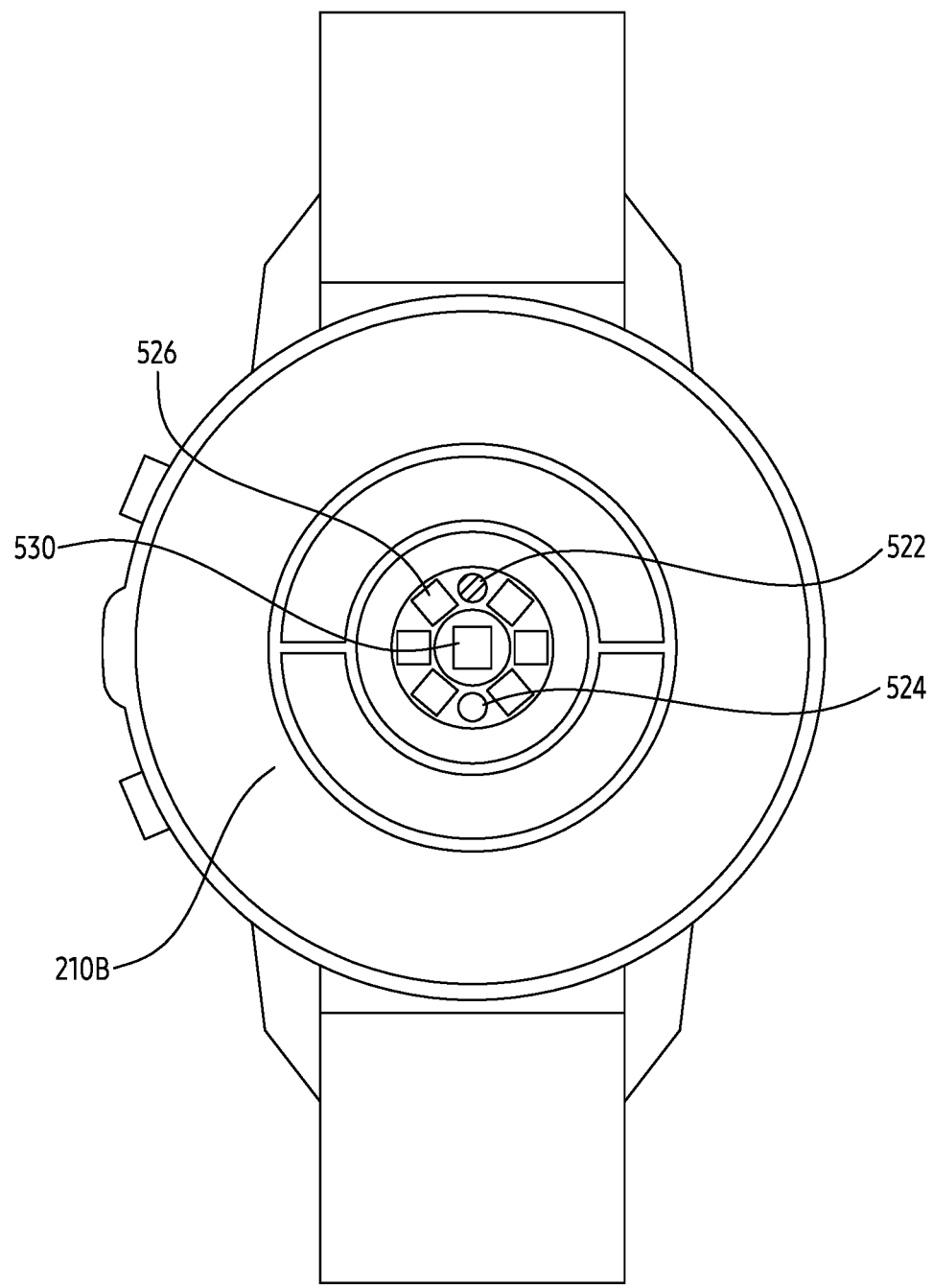
FIG. 5B illustrates a rear surface of an electronic device in which a sensor module is embedded according to various embodiments.

FIG. 5A is a block diagram of a sensor module 211 according to various embodiments and FIG. 5B illustrates a rear surface 210B of an electronic device 101 in which the sensor module 211 is embedded according to various embodiments.

Referring to FIG. 5A, the sensor module 211 may include at least one sensor. For example, the sensor module 211 may include at least an inertia sensor 510, a photoplethysmogram (PPG) sensor 520, a body temperature sensor 530, or a bio electrode sensor 540.

According to an embodiment, the inertia sensor 510 may further include an acceleration sensor (not shown), a gyro sensor (not shown), and/or a geomagnetic sensor (not shown). The inertia sensor 510 may obtain acceleration components in the x-axis, y-axis, and z-axis directions based on the acceleration sensor (not shown), and may identify a rotating angular speed when the electronic device 101 rotates based on the gyro sensor (not shown). In addition, the inertia sensor 510 may compensate for an error with respect to a movement of the electronic device 101 measured by the acceleration sensor (not shown) and the gyro sensor (not shown) using the geomagnetic sensor (not shown).

According to an embodiment, the PPG sensor 520 may obtain biometric data based on optical information. The biometric data may include at least one of a heart rate, a change in a user's heart rate during a predetermined time, an oxygen saturation degree, and a blood pressure. According to an embodiment, the PPG sensor 520 may face a part of the user's body when the electronic device 101 is worn by the user. The PPG sensor 520 may emit light toward the user's body and receive light reflected from the user's body in order to detect a change in blood flow in a microvasculature. In the user's body, due to periodic contraction or relaxation of the heart, the amount of blood flow in the microvasculature may change, and thus the volume of the microvasculature may also change. The amount of light emitted toward the user's body is absorbed into the body may vary according to the amount of blood flow in the microvasculature. The PPG sensor 520 may obtain biometric data based on intensity of light reflected from the user's body.

Referring to FIG. 5B, the PPG sensor 520 may include at least one light emitting device 522, 524 and at least one light receiving device 526. For example, the at least one light emitting device may include a light emitting diode 522 outputting green light, a light emitting diode 524 outputting red light, and a light emitting diode (not shown) outputting infrared light. At least one light receiving device 526 may correspond to a photodiode for receiving light output from at least one light emitting device 522 and 524. For example, at least one light receiving device 526 may be disposed based on a center point of the rear surface 210B of the electronic device 101.

According to an embodiment, the bio electrode sensor 540 may measure the heart rate by measuring an electrical signal generated by the heart, measure the body composition by analyzing the difference in impedance of biological tissues constituting the body, and measure a stress information by measuring electro dermal activity (EDA) by using sweat secretion based on sympathetic nerve.

According to various embodiments, the body temperature sensor 530 may measure the temperature of the user's body. According to an embodiment, the body temperature sensor 530 may be implemented as a non-contact type sensor. The non-contact type sensor may measure the temperature without contacting the user's body. For example, the non-contact type sensor may correspond to an infrared thermometer. The body temperature sensor 530 of the non-contact type sensor may measure the temperature with an infrared radiation rate. According to an embodiment, the body temperature sensor 530 may further include a lens (not shown) for receiving infrared light. The body temperature sensor 530 corresponding to the infrared thermometer may compensate for an error based on the peripheral temperature of the electronic device 101 and convert it into an electrical signal that may be displayed in a temperature unit.

According to an embodiment, the body temperature sensor 530 may be implemented as a contact type sensor. The contact type sensor may measure the temperature of the user's body by contacting the user's body. For example, at least a thermocouple, a resistance temperature sensor (RTD), and a thermistor may be included. The resistance temperature sensor and the thermistor may measure a temperature by measuring a resistance value that varies according to a temperature change. The thermocouple temperature sensor may connect different types of metals and measure a temperature according to a current value that varies according to a temperature change. The contact type sensor may be classified into a skin temperature sensor, a body temperature sensor, and a core body temperature sensor according to a measurement target. The body temperature sensor 530 according to an embodiment may refer to a sensor for measuring the forehead, the armpit, and/or the inside of the mouth, which is a part measured via a thermometer according to the comparative embodiment, but is not limited thereto. For example, the body temperature sensor 530 may include both the skin temperature sensor for measuring the temperature of the epidermis and the core body temperature sensor for measuring the temperature of the internal organs.

Figure 6:
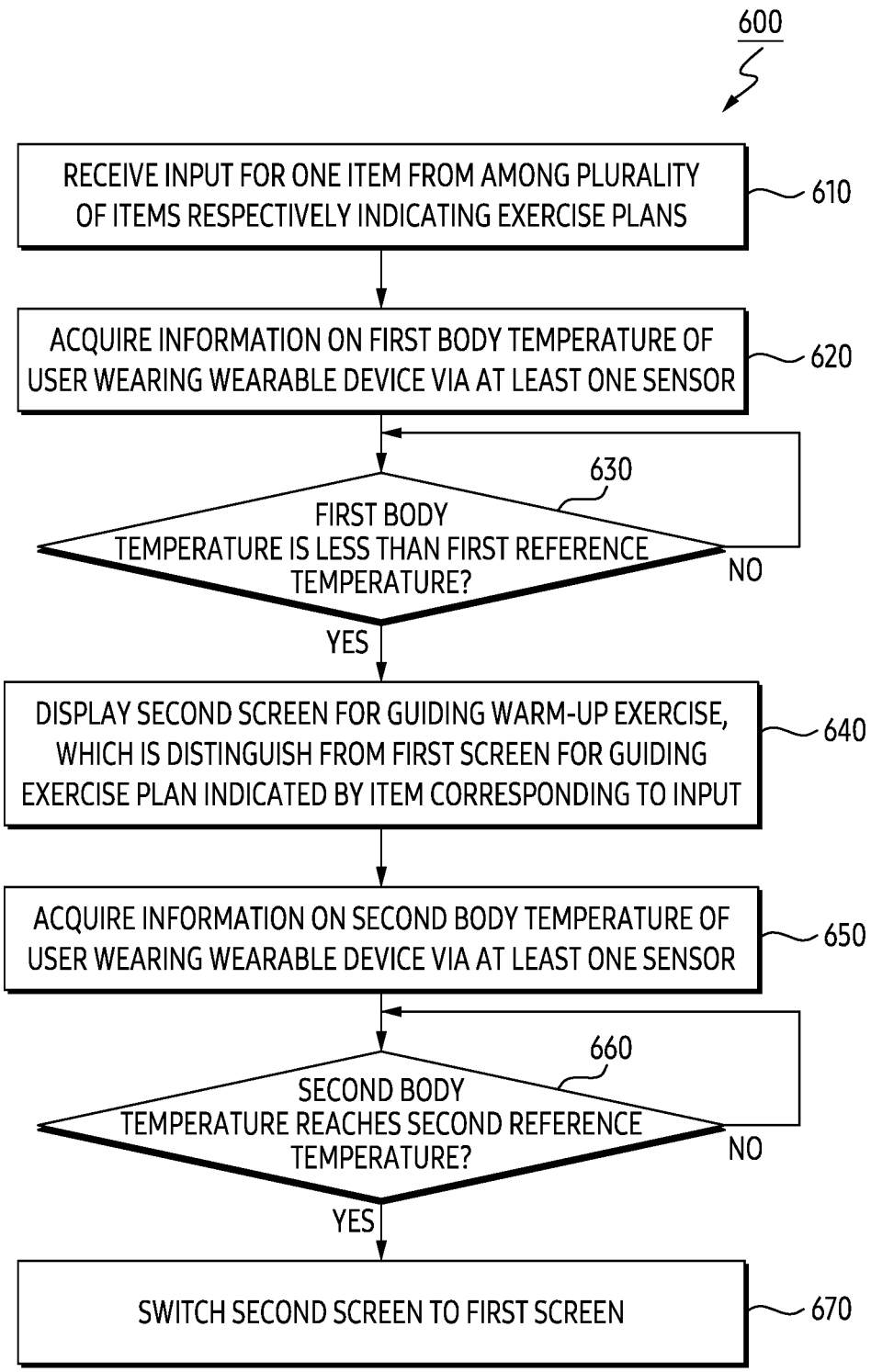
FIG. 6 is a flowchart illustrating an operation of an electronic device for guiding a warm-up exercise according to various embodiments.

FIG. 6 is a flowchart illustrating an operation of an electronic device 101 for guiding a warm-up exercise according to various embodiments.

Figure 7A:
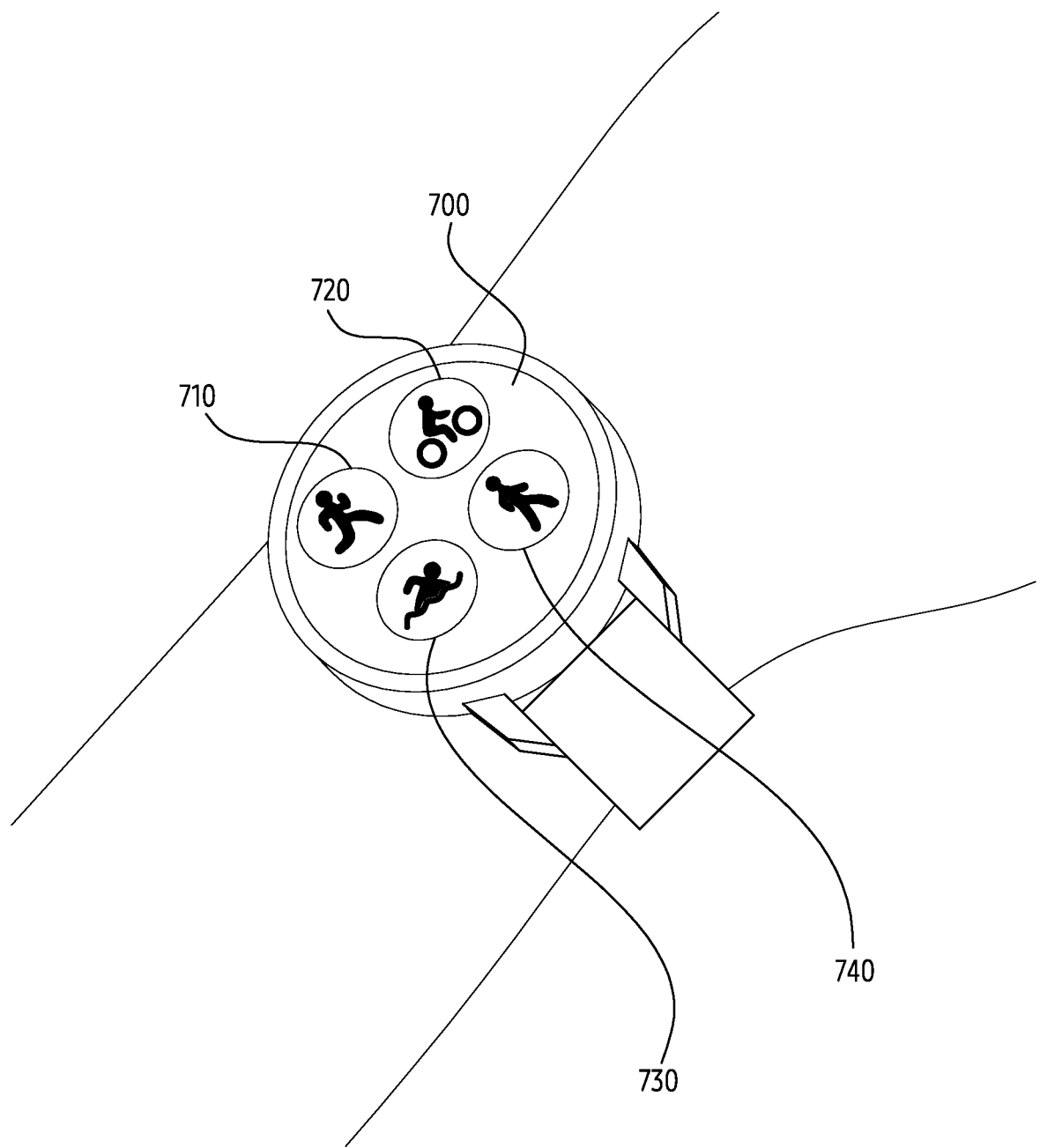
FIG. 7A illustrates an example of a display displaying a plurality of items according to various embodiments.

FIG. 7A illustrates an example of a display displaying a plurality of items according to various embodiments.

Figure 7B:
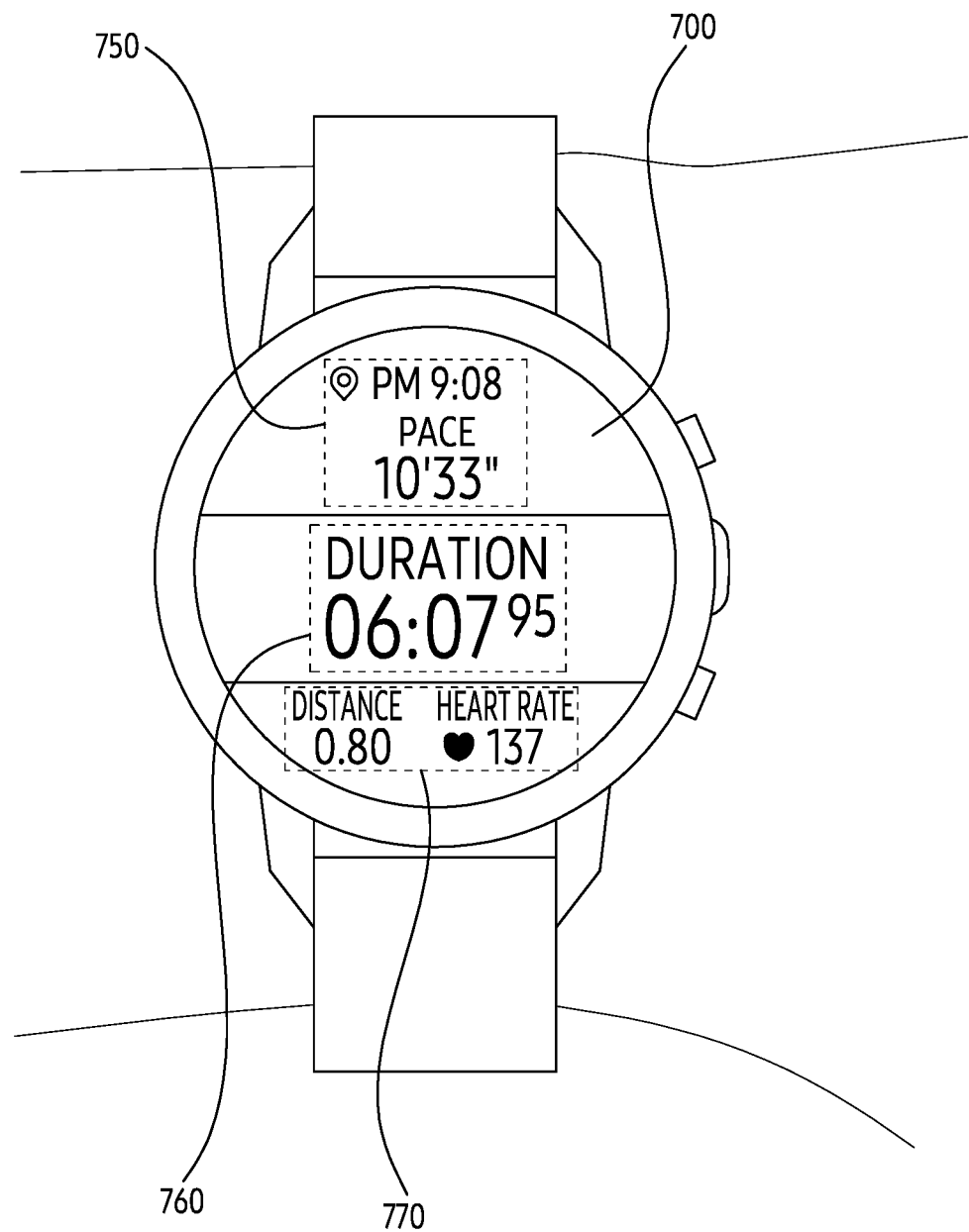
FIG. 7B illustrates an example of a display displaying a first screen according to various embodiments.

FIG. 7B illustrates an example of a display displaying a first screen according to various embodiments.

Figure 8A:
FIG. 8A illustrates an example of a display displaying a second screen according to various embodiments.

FIG. 8A illustrates an example of a display displaying a second screen according to various embodiments.

Figure 8B:
FIG. 8B illustrates another example of a display displaying a second screen according to various embodiments.

FIG. 8B illustrates another example of a display displaying a second screen according to various embodiments.

Figure 8C:
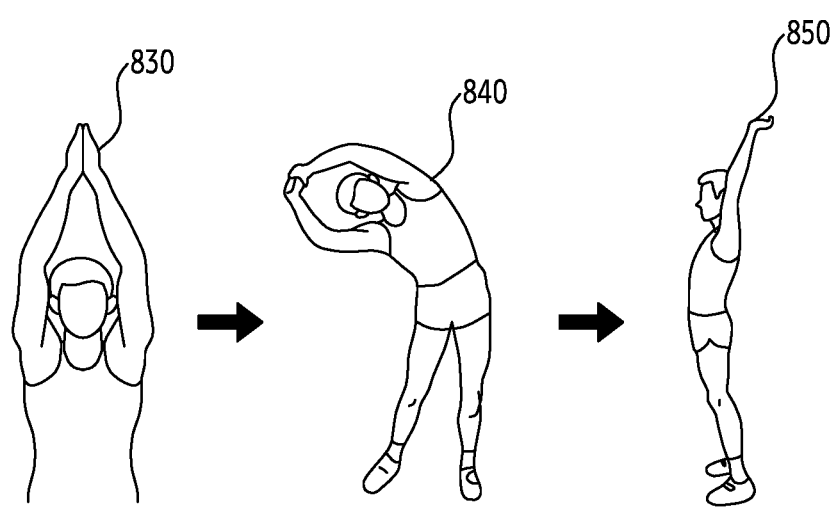
FIG. 8C illustrates another example of a display displaying a second screen according to various embodiments.

FIG. 8C illustrates another example of a display displaying a second screen according to various embodiments.

Referring to FIG. 6, in operation 610, the processor 120 may receive an input for one item among a plurality of items respectively indicating exercise plans. The exercise plan may indicate a type of exercise that may be performed by a user wearing the electronic device 101. The exercise plan may be referred to in various terms such as an exercise routine and/or an exercise program. Referring to FIG. 7A together, the display 700 (e.g., the display 220 of FIG. 3) may display a plurality of items 710, 720, 730, and 740. Each of the plurality of items 710, 720, 730, and 740 may include a visual object of a representative pictogram so that a user may intuitively distinguish the exercise plan. For example, the first item 710 may include a visual object of a pictogram corresponding to running. The second item 720 may include a visual object of a pictogram corresponding to a bicycle riding. The third item 730 may include a visual object of a pictogram corresponding to swimming. The fourth item 740 may include a visual object of a pictogram corresponding to walking. The processor 120 may receive a user input via a touch-sensitive interface of the display 220 and identify which exercise the user of the electronic device 101 wants to perform. For example, the processor 120 may identify to guide a running exercise corresponding to a user input to the first item 710.

In operation 620, the processor 120 may obtain information on a first body temperature of a user wearing a wearable device (e.g., an electronic device 101) via at least one sensor. The wearable device may correspond to the electronic device 101 illustrated in FIG. 1, the electronic device 200 illustrated in FIG. 2A, and the electronic device 300 illustrated in FIG. 3. The processor 120 may identify the first body temperature at the selected time point in response to a user selecting the first item 710 from among a plurality of items 710, 720, 730, and 740.

In operation 630, the processor 120 may determine whether the first body temperature is less than the first reference temperature. The first reference temperature may be a temperature for determining whether the user needs to perform a warm-up exercise. For example, when the first body temperature at the time of receiving the user input to the first item 710 among the plurality of items 710, 720, 730, and 740, is higher than the first reference temperature, the processor 120 may determine that the first body temperature is higher than the first reference temperature since the user has performed a separate warm-up exercise or has completed stretching. The processor 120 may immediately display a first screen for guiding the main exercise (e.g., running) without guiding the warm-up exercise.

For another example, when the first body temperature at the time of receiving the user input to the first item 710 among the plurality of items 710, 720, 730, and 740 is lower than the first reference temperature, the processor 120 may identify that the user of the electronic device 101 wants to immediately perform the main exercise (e.g., running) without performing warm-up exercise or stretching. When the first body temperature is lower than the first reference temperature, the processor 120 may determine that there is a considerable risk of injury because the exercise starts immediately without performing sufficient warm-up exercise or stretching.

In operation 640, the processor 120 may display a second screen for guiding the warm-up exercise distinguished from a first screen for guiding the exercise plan indicated by an item corresponding to an input. For example, referring to FIG. 7B together, the display 700 may display a first screen. The first screen may display a plurality of visual objects guiding an exercise plan indicated by an item corresponding to an input. For example, the first screen may include a first visual object 750, a second visual object 760, and/or a third visual object 770. For example, the first visual object 750 may include objects displaying the current time and/or the pace of the current running exercise. For example, the second visual object 760 may include objects indicating the elapsed time of the exercise plan indicated by the item corresponding to the input. For example, the third visual object 770 may include objects displaying biometric data (e.g., current heart rate) and/or movement distance of the user.

According to various embodiments, the processor 120 may bypass displaying the first screen and display a second screen different from the first screen. The second screen may be a screen for guiding a warm-up exercise. For example, although the first visual object 750, the second visual object 760, and/or the third visual object 770 of FIG. 7B should be displayed, the processor 120 may display a second screen different from the first screen of FIG. 7B since the exercise plan indicated by the item corresponding to the input is running.

Referring to FIG. 8A, the processor 120 may display a second screen in response to identifying a first body temperature lower than the first reference temperature. The second screen may include a visual object 810 for notifying that a warm-up exercise starts. For example, visual object 810 may include phrases to indicate that a warm-up exercise is initiated, such as "start a warm-up exercise to prevent injury," "start a warm-up exercise," and/or "start a warming-up."

Referring to FIG. 8B, the processor 120 may display a second screen in response to identifying a first body temperature lower than the first reference temperature. The second screen may include a visual object 820 requesting a user input whether to perform a warm-up exercise. For example, the visual object 820 may include phrases requesting user input, such as "Do you want to start warm-up exercise?" and/or "Press Yes to start warm-up exercise". When a user input is received via an object corresponding to "Yes", the processor 120 may display the first screen of FIG. 8A or the object guiding the warm-up exercise of FIG. 8C. When a user input is received via an object corresponding to "No", the processor 120 may display the first screen of FIG. 7B.

Referring to FIG. 8C, the processor 120 may display objects guiding a warm-up exercise. For example, the processor 120 may display the object 830 via the display 220. The object 830 may be an object that guides a warm-up exercise for relaxing the shoulder muscles of the user. According to various embodiments, the processor 120 may display the object 840 and the object 850 over a time flow. For example, the processor 120 may identify whether a movement based on a guide of the object 830 is detected via the inertia sensor 510, and may display the object 840 of the next order when the movement based on the guide of the object 830 is detected.

In operation 650, the processor 120 may obtain information on the second body temperature of the user wearing the wearable device via at least one sensor. The second body temperature may correspond to the user's body temperature measured while the second screen is displayed via the display 220. For example, referring to FIG. 8C together, visual objects 830, 840, and 850 for guiding the posture and/or the number of warm-up exercises may be displayed via the second screen. The user may perform a warm-up exercise based on the guide of the second screen. As the user performs a warm-up exercise, the user's body temperature may increase.

In operation 660, the processor 120 may identify whether the second body temperature reaches the second reference temperature. The second reference temperature may be a temperature that determines an end the warm-up exercise. For example, the second reference temperature may be a temperature higher than the first reference temperature.

In an embodiment, the second reference temperature may be fixedly set to a designated temperature value. For example, the second reference temperature may be a fixed value as 38° C. The processor 120 may end the warm-up exercise in response to identifying that the second body temperature reaches about 38° C., which is an example of the second reference temperature.

In another embodiment, the second reference temperature may be variably set. The second reference temperature may be determined based on the first body temperature. For example, since the risk of injury when the first body temperature is low (e.g., 35° C. to 36° C.) is greater than when the body temperature is higher, the second reference temperature for ending the warm-up exercise may be set higher. For example, the second reference temperature may be set to a temperature that has risen by about 2° C. based on the first body temperature in order to induce sufficient warm-up exercise. For another example, since the risk of injury when the first body temperature is high (e.g., 37° C.) is lower than when the first body temperature is low, the second reference temperature for ending the warm-up exercise may be set low. For example, the second reference temperature may be set to a temperature that risen by about 1° C. based on the first body temperature in order to induce a warm-up exercise of appropriate intensity. According to an embodiment, the second reference temperature may be variably set based on the intensity of the exercise plan indicated by an item corresponding to an input. For example, when the exercise plan indicated by the item corresponding to the above input is running and the target distance is 30 Km, a large amount of warm-up exercise may be required to lower the risk of injury than when the target distance is 5 Km. Accordingly, the processor 120 may induce sufficient warm-up exercise by setting the second reference temperature higher.

In another embodiment, the second reference temperature may be determined based on an external temperature of the electronic device 101. According to various embodiments, the processor 120 may obtain information on an external environment of the electronic device 101 via the sensor module 176. For example, the processor 120 may obtain information on the external temperature and the external humidity of the electronic device 101 via the temperature sensor and the humidity sensor included in the sensor module 176. For example, in the case of cold weather in which the external temperature is 10° C. or less, the second reference temperature may be set to a temperature about 1° C. higher than the first body temperature. For example, in the case of warm weather in which the external temperature is 30° C. or more, the second reference temperature may be set to a temperature about 0.5° C. higher than the first body temperature.

According to an embodiment, the second reference temperature may be varied based on personal information of the user of the electronic device 101. The personal information may refer to information capable of specifying a user, such as the user's age, gender, job, and/or residence. The electronic device 101 may variably set the second reference temperature in consideration of the body temperature average for each time zone according to statistics based on the personal information. For example, the second reference temperature for determining that sufficient warm-up exercise has been completed may be set higher for a female user than for a male user. For another example, the second reference temperature may be variably set to be proportional to the age of the user.

In operation 670, the processor 120 may switch the second screen to the first screen. When the body temperature rises to reach the second reference temperature according to performing the warm-up exercise shown in FIG. 8C, the processor 120 may identify that the user is ready to perform the main exercise (e.g., running). The processor 120 may change the second screen displayed via the display 220. The processor 120 may display a first screen corresponding to an input for one item among a plurality of items received in operation 610. For example, when the user selects the first item 710 from among a plurality of items 710, 720, 730, and 740, the processor 120 may display a first screen for running corresponding to the first item 710. For example, the first screen may include a first visual object 750 of FIG. 7B, a second visual object 760, and/or a third visual object 770.

Figure 9:
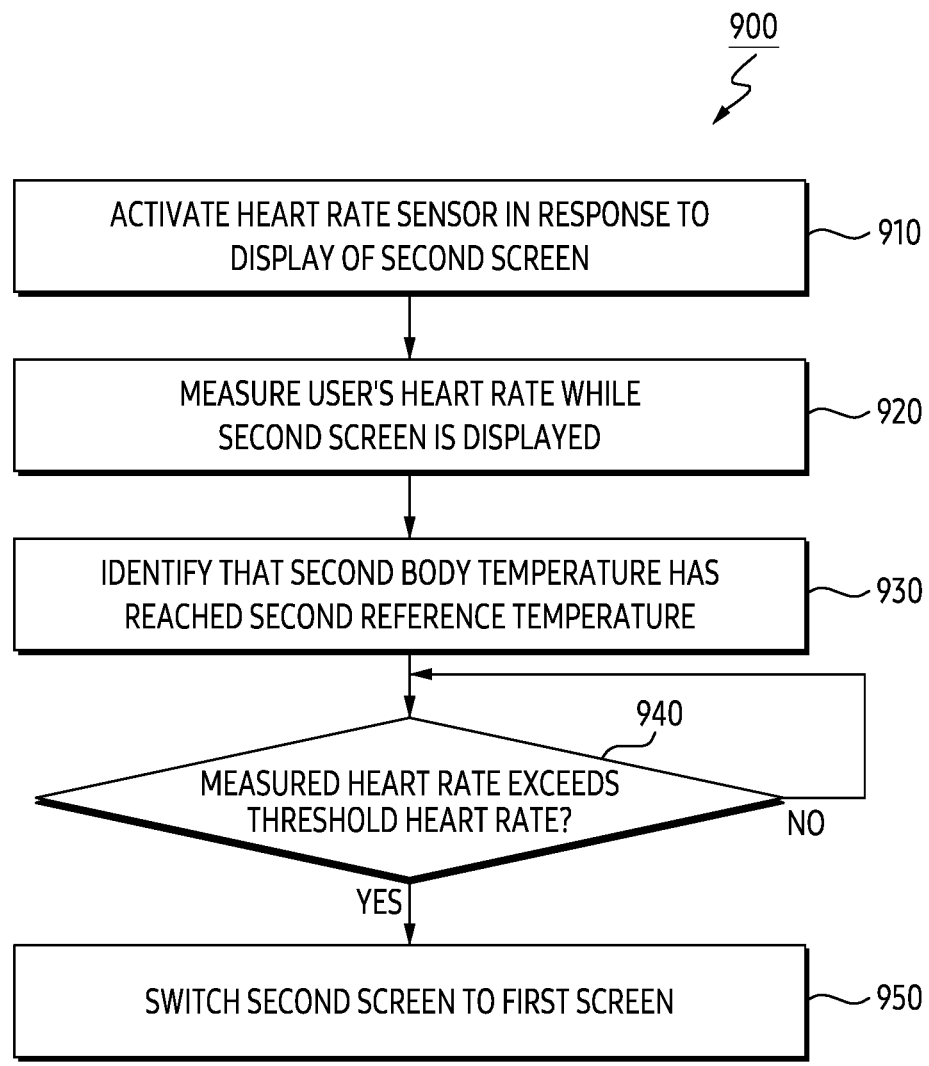
FIG. 9 is a flowchart illustrating an operation of an electronic device for guiding a warm-up exercise according to various embodiments.

FIG. 9 is a flowchart illustrating an operation of an electronic device 110 for guiding a warm-up exercise according to various embodiments.

In operation 910, the processor 120 may activate a heart rate sensor in response to the display of the second screen. The heart rate sensor is a sensor for measuring a user's heart rate, and may correspond to at least one of the PPG sensor 520 and the bio electrode sensor 540.

In operation 920, the processor 120 may measure the user's heart rate while the second screen is displayed. As the user performs a warm-up exercise guided via the second screen, the measured heart rate while the second screen is displayed may increase. The measurement of the heart rate may be performed via the PPG sensor 520. According to an embodiment, in response to identifying displaying the second screen for guiding the warm-up exercise, while measuring the heart rate via the PPG sensor 520, the processor 120 may set the sensing sensitivity of the PPG sensor 520 to be high. This is because the user does not have sufficient physical activity before performing the warm-up exercise, so the blood flow at the time of the warm-up exercise may not be sufficient to measure the heart rate. For example, the processor 120 may set a short measurement period of the PPG sensor 520 to increase the sensing sensitivity of the PPG sensor 520. For another example, the processor 120 may increase the sensing sensitivity of the PPG sensor 520 by increasing the amount of light output from the light emitting devices 522 and 524.

In operation 930, the processor 120 may identify that the second body temperature reaches the second reference temperature. Operation 930 may correspond to operation 660 of FIG. 6.

In operation 940, the processor 120 may identify whether the measured heart rate exceeds the threshold heart rate. The threshold heart rate may be a value for determining whether to end the second screen for guiding the warm-up exercise. For example, when the user sufficiently performs a warm-up exercise according to the second screen, the measured heart rate may exceed a threshold heart rate.

According to an embodiment, when the heart rate measured in operation 940 is less than the threshold heart rate, the processor 120 may continuously monitor the user's heart rate based on the heart rate sensor.

According to another embodiment, when the measured heart rate in operation 940 exceeds the threshold heart rate, the processor 120 may perform operation 950 to switch from the second screen to the first screen. That is, the processor 120 may identify that the heart rate exceeds the threshold heart rate in addition to the second reference temperature exceeding because the user has sufficiently performed a warm-up exercise. That is, the processor 120 may determine that the processor 120 is ready to perform the main exercise (e.g., running) based on both the body temperature and the heart rate.

In the above-described embodiment, the processor 120 is described as determining whether the heart rate measured after operation 930 of identifying that the second body temperature reaches the second reference temperature exceeds the threshold heart rate, but is not limited thereto. The processor 120 may measure body temperature and heart rate at substantially the same time and determine whether a condition for ending the second screen has been achieved, respectively. For example, the processor 120 may determine whether the second body temperature exceeds the second reference temperature and whether the measured heart rate exceeds the threshold heart rate substantially simultaneously and in parallel.

Figure 10:
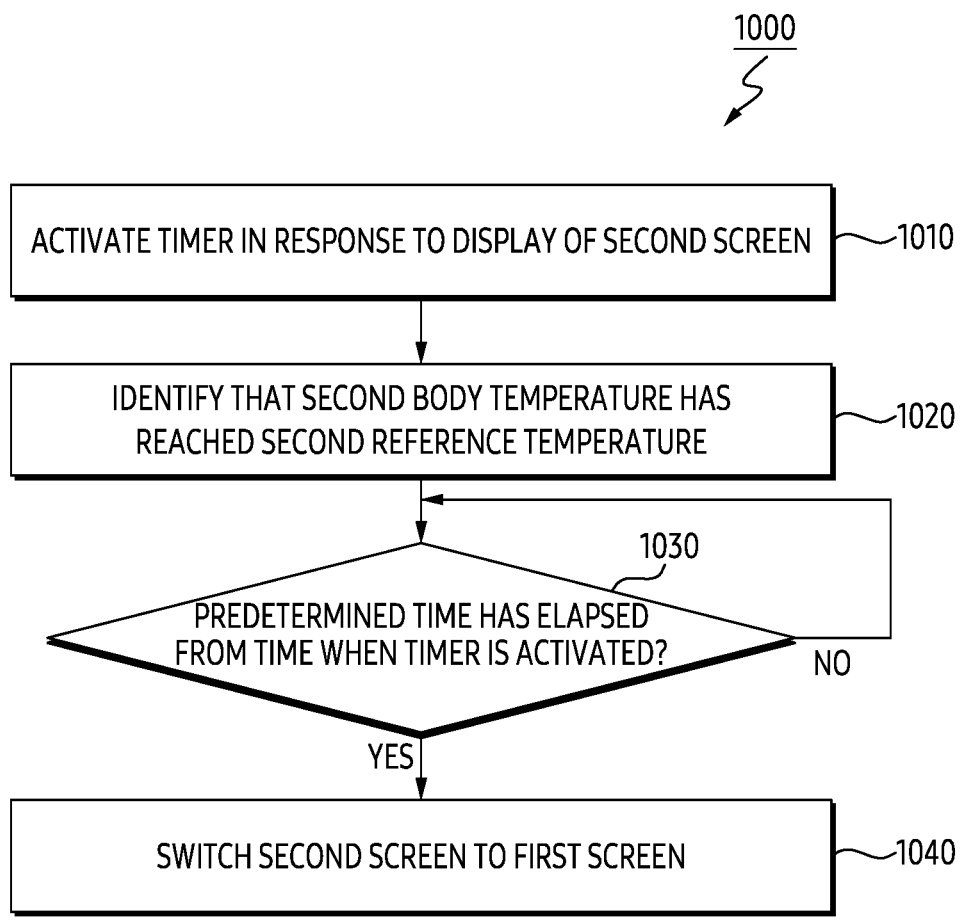
FIG. 10 is a flowchart illustrating an operation of an electronic device for guiding a warm-up exercise according to various embodiments.

FIG. 10 is a flowchart illustrating an operation of an electronic device 101 for guiding a warm-up exercise according to various embodiments.

Referring to FIG. 10, in operation 1010, the processor 120 may activate a timer in response to the display of the second screen. The timer may be for determining whether a predetermined time elapses from a time point at which the second screen is displayed.

According to an embodiment, the predetermined time may have a fixed length. For example, the predetermined time may be set to 5 minutes. In this case, the processor 120 may display the second screen for at least 5 minutes.

According to another embodiment, the predetermined time may have a variable length. The predetermined time may be variably set based on an external temperature of the electronic device 101. For example, when the external temperature is cold weather of 10° C. or less, the predetermined time may be set longer to 10 minutes. For another example, when the external temperature is warm weather of 30° C. or higher, the predetermined time may be set shorter as 3 minutes. In addition, when the external humidity is too high, the predetermined time may be briefly set to 3 minutes. According to an embodiment, the predetermined time may be variably set based on the intensity of the exercise plan indicated by an item corresponding to a user input. For example, when the exercise plan indicated by the item corresponding to the user input is running and the target distance is 30 Km, a large amount of warm-up exercise may be required to lower the risk of injury than when the target distance is 5 Km. Accordingly, the processor 120 may induce a sufficient warm-up exercise by setting the predetermined length of time to be longer.

In operation 1020, the processor 120 may identify that the second body temperature reaches the second reference temperature. Operation 1020 may correspond to operation 660 of FIG. 6.

In operation 1030, the processor 120 may identify whether a predetermined time has elapsed from the time point when the timer is activated. When a predetermined time has not elapsed from the time point when the second screen is displayed, the processor 120 may continuously display the second screen. For example, when the predetermined time has not elapsed, the processor 120 may continue to display the second screen via the display 220 even when the second body temperature reaches the second reference temperature. For another example, when the predetermined time has elapsed, the processor 120 may switch the second screen to the first screen in operation 1040. Operation 1040 may correspond to operation 950 of FIG. 9.

In the above-described embodiment, the processor 120 is described as determining whether a predetermined time elapses from the time point at which the timer is activated after the operation 1020 identifying that the second body temperature reaches the second reference temperature, but is not limited thereto. The processor 120 may identify that the predetermined time has elapsed before the second body temperature reaches the second reference temperature. When the predetermined time has elapsed, but the second body temperature has not reached the second reference temperature, the processor 120 may display the second screen until the second body temperature reaches the second reference temperature.

Figure 11A:
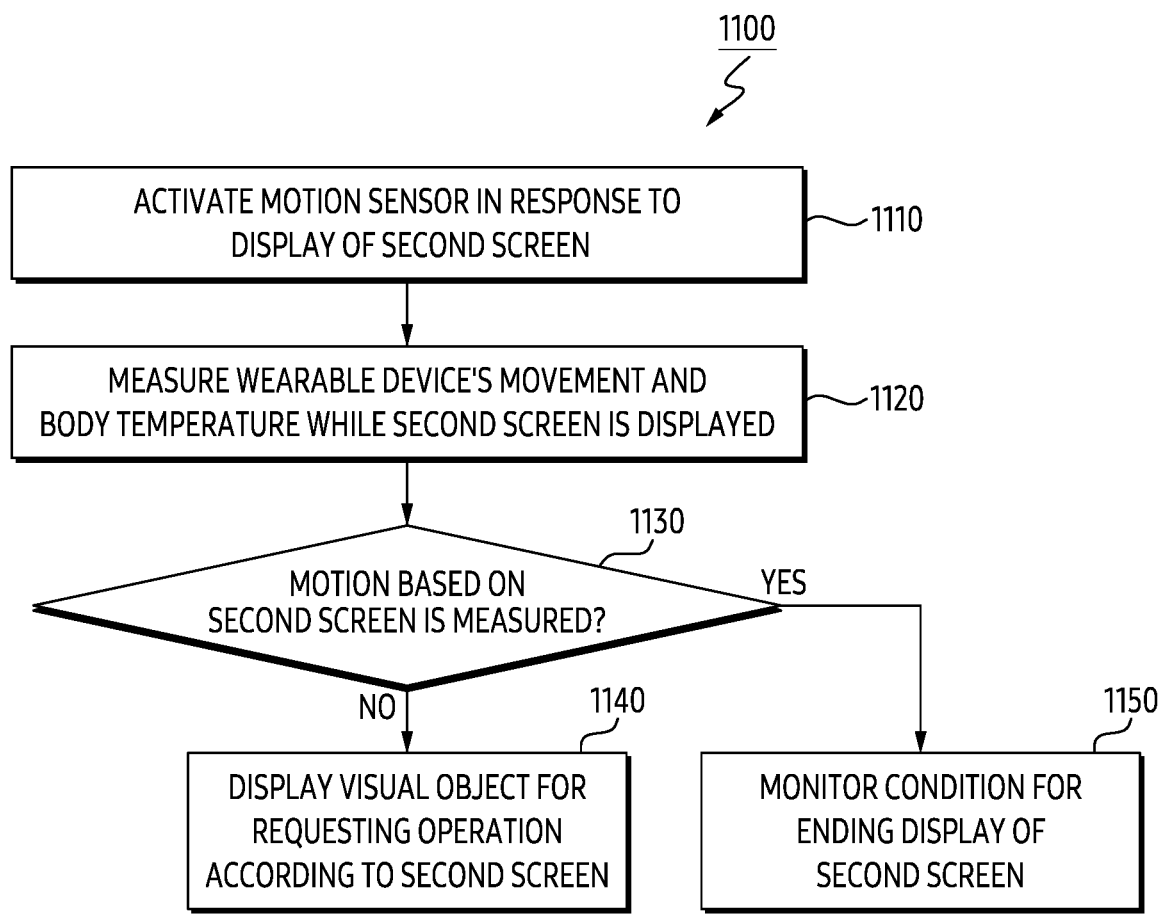
FIG. 11A is a flowchart illustrating an operation of an electronic device for guiding a warm-up exercise according to various embodiments.

FIG. 11A is a flowchart illustrating an operation of an electronic device 101 for guiding a warm-up exercise according to various embodiments.

Figure 11B:
FIG. 11B is an example of a visual object for requesting an operation according to a second screen according to various embodiments.

FIG. 11B is an example of a visual object for requesting an operation according to a second screen according to various embodiments.

Referring to FIG. 11A, in operation 1110, the processor 120 may activate the motion sensor in response to the display of the second screen. The motion sensor is for identifying whether the user performs a warm-up exercise guided according to the second screen, and may be a sensor for measuring the user's movement. For example, the motion sensor may correspond to the inertia sensor 510 of FIG. 5A. According to an embodiment, the processor 120 may activate a gyro sensor (not shown) among motion sensors (e.g., the inertia sensor 510) in response to the display of the second screen. The acceleration sensor (not shown) of the motion sensor (e.g., the inertia sensor 510) may operate in an activated state even before the display of the second screen. When the processor 120 detects whether to perform an operation of the objects 830, 840, and 850 indicating a warm-up exercise to be displayed via the second screen using sensing data obtained via an acceleration sensor (not shown), the detection accuracy may be degraded. Accordingly, the processor 120 may further activate a gyro sensor (not shown) among motion sensors (e.g., the inertia sensor 510) in response to the display of the second screen.

In operation 1120, the processor 120 may measure a movement of the wearable device (e.g., the electronic device 101) while the second screen is displayed. For example, the processor 120 may display the operation of the object 830 of FIG. 8C via the second screen. When the user of the electronic device 101 moves along the object 830 displayed on the display 220, the processor 120 may measure the movement using a motion sensor (e.g., the inertia sensor 510 of FIG. 5A). According to an embodiment, the processor 120 may obtain and store a sensing data set for detecting a user's movement of the electronic device 101 using an acceleration sensor (not shown) and a gyro sensor (not shown) of a motion sensor (e.g., the inertia sensor 510).

In operation 1130, the processor 120 may identify whether a movement based on the second screen is measured. For example, the processor 120 may display the object 830 of FIG. 8C via the display 220. The processor 120 may determine whether the movement measured in operation 1120 included in the obtained sensing data set matches the movement of the electronic device 101 when the object 830 is a warm-up exercise. For example, the processor 120 may analyze a data pattern based on the sensing data set. The processor 120 may identify whether the movement based on the second screen is measured based on whether the data pattern corresponding to the operation of the object 830 displayed on the display 220 is included in the sensing data set. When the expected movement of the electronic device 101 based on the operation of the object 830 displayed on the screen and the movement measured in operation 1120 are different from each other or there is no movement measured in operation 1120, the processor 120 may request the user to perform a warm-up exercise again.

In operation 1140, the processor 120 may display a visual object for requesting an operation according to the second screen. For example, referring to FIG. 11B together, the processor 120 may display the visual object 1160 via the display 700. The visual object 1160 may include a phrase for requesting a user to perform a warm-up exercise. For example, the phrase may be a request phrase such as, "Please perform a warm-up exercise to prevent injury." According to various embodiments, the visual object 1160 may further include objects for receiving user selection. For example, in case the user no longer wants to perform a warm-up exercise, the visual object 1160 may further include an object for "no (skip)." When the user selects the "no (skip)" object, the processor 120 may switch the second screen corresponding to the screen displayed via the display 220 to the first screen in response to the selection.

In operation 1150, the processor 120 may monitor a condition for ending the display of the second screen. For example, the processor 120 may end the display of the second screen in response to monitoring the second body temperature and identifying that the second body temperature reaches the second reference temperature. For example, the processor 120 may additionally identify whether the measured heart rate exceeds the threshold heart rate in response to the second body temperature reaching the second reference temperature. The processor 120 may measure the body temperature and the heart rate substantially simultaneously and determine whether conditions for ending the second screen are achieved, respectively. For example, the processor 120 may substantially simultaneously and in parallel determine whether the second body temperature exceeds the second reference temperature and whether the measured heart rate exceeds the threshold heart rate.

Figure 12:
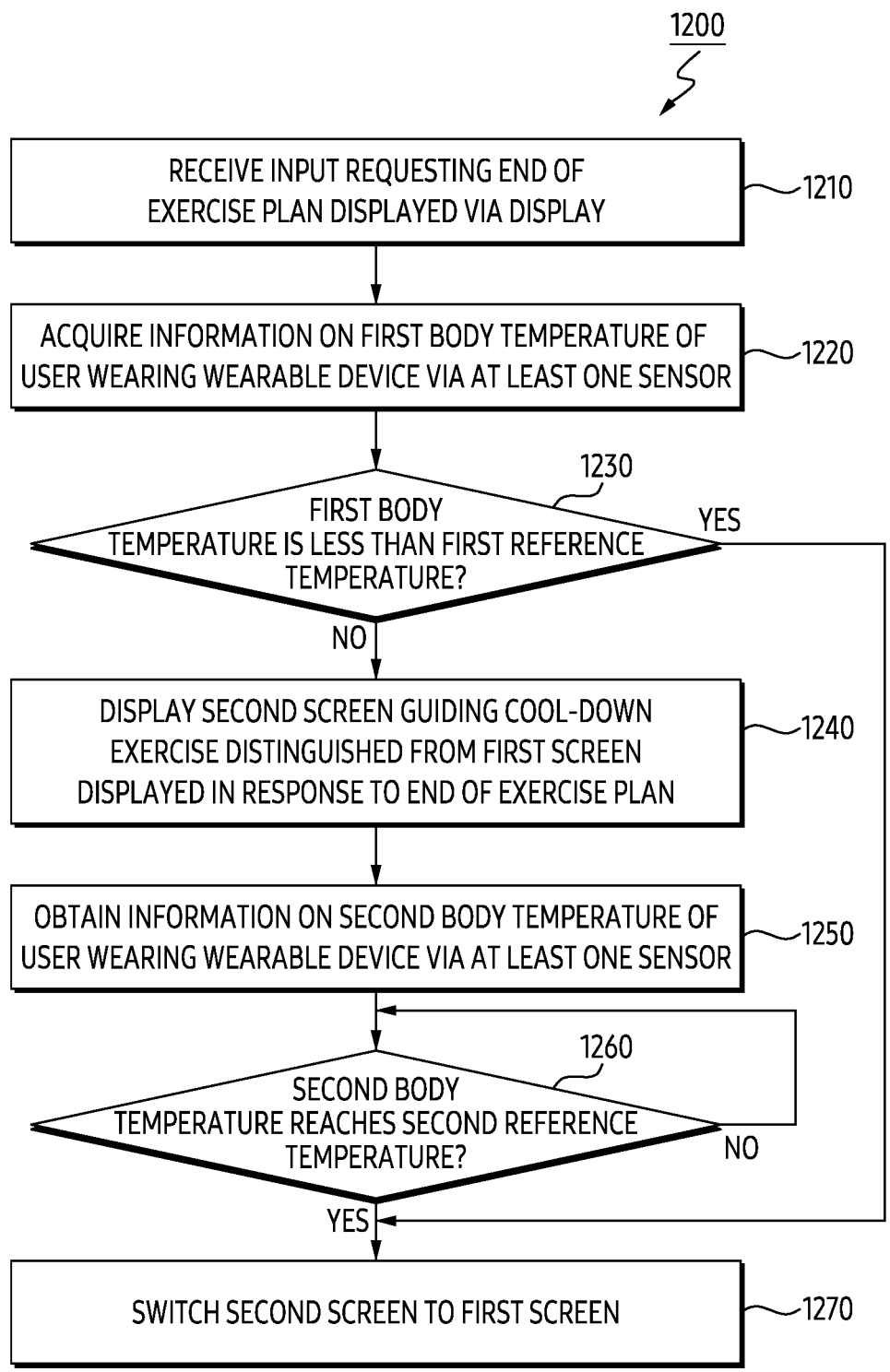
FIG. 12 is a flowchart illustrating an operation of an electronic device for guiding a cooling-down exercise according to various embodiments.

FIG. 12 is a flowchart illustrating an operation of an electronic device 101 for guiding a cooling-down exercise according to various embodiments.

Figure 13A:
FIG. 13A illustrates an example of requesting an end of an exercise plan according to various embodiments.

FIG. 13A illustrates an example of requesting an end of an exercise plan according to various embodiments.

Figure 13B:
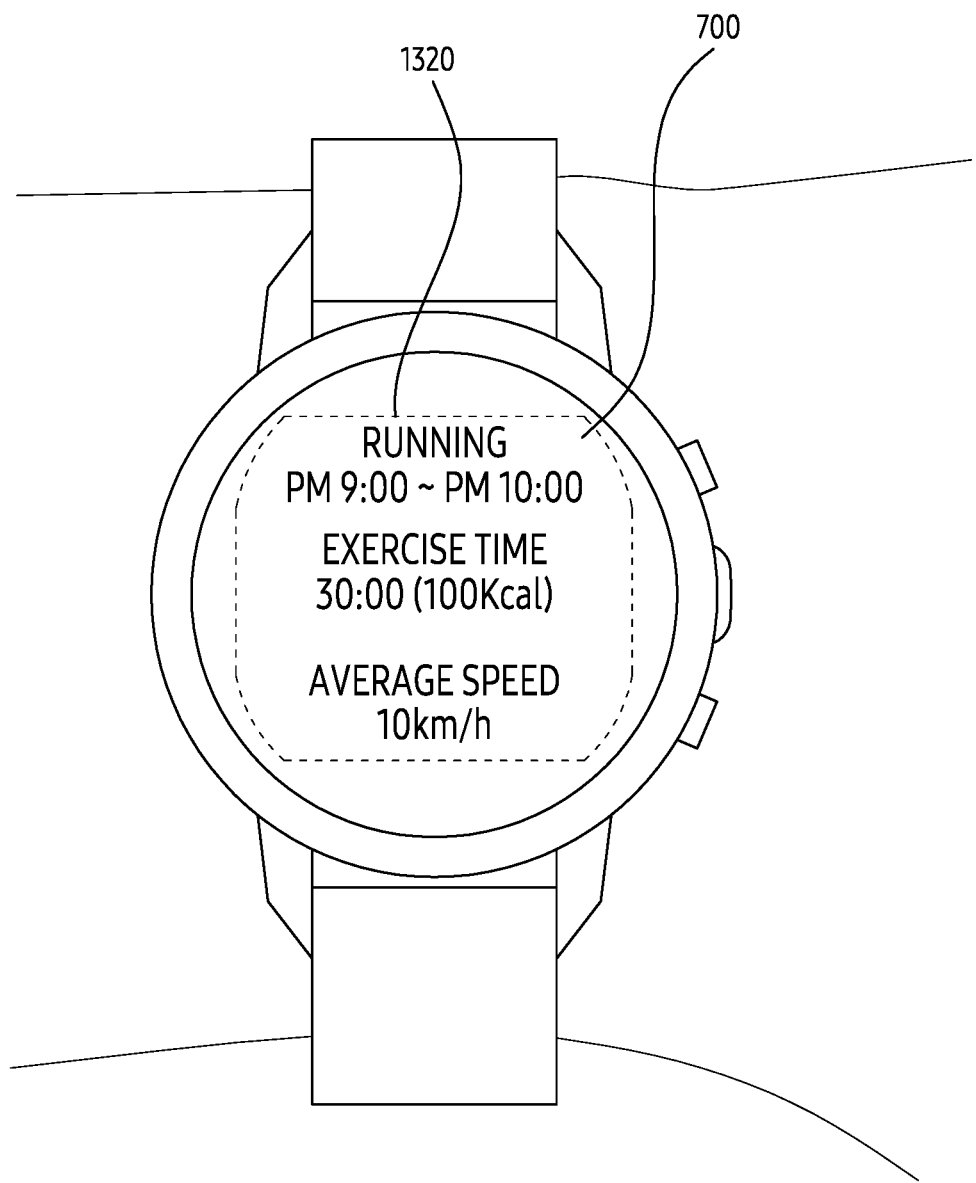
FIG. 13B illustrates an example of a display displaying a first screen according to various embodiments.

FIG. 13B illustrates an example of a display displaying a first screen according to various embodiments.

Figure 13C:
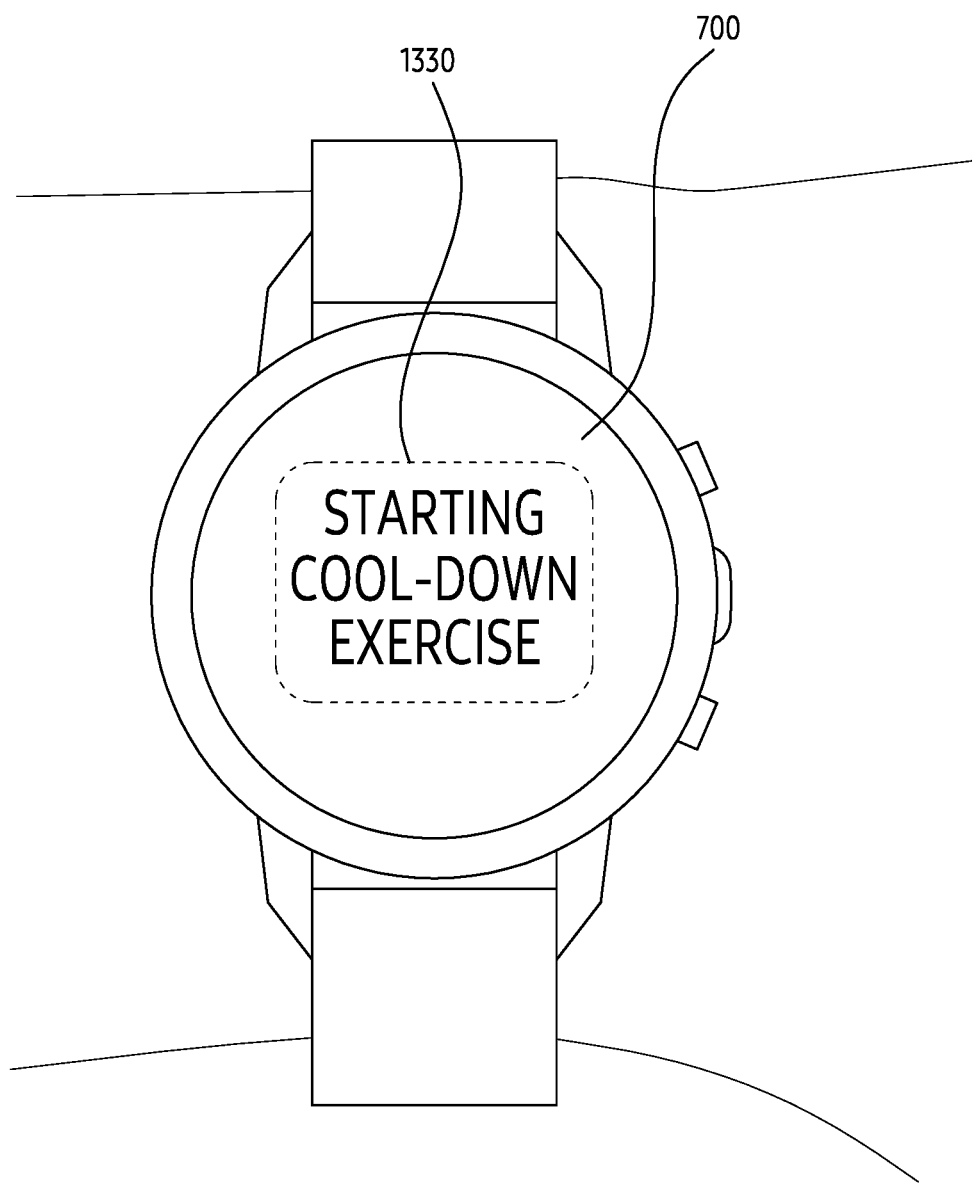
FIG. 13C illustrates another example of a display displaying a second screen according to various embodiments.

FIG. 13C illustrates another example of a display 220 displaying a second screen according to various embodiments.

Referring to FIG. 12, in operation 1210, the processor 120 may receive an input for requesting the end of the exercise plan displayed via the display 220. Referring to FIG. 7A together, the exercise plan may be an exercise corresponding to one item requested by a user among a plurality of items 710, 720, 730, and 740 displayed on the display 700 (e.g., the display 220 of FIG. 3). For example, the processor 120 may guide a running exercise corresponding to a user input to the first item 710. Referring to FIG. 13A together, the processor 120 may receive an input for requesting the end of the exercise plan. For example, the processor 120 may display the visual object 1310 via the display 700. The visual object 1310 may include a phrase requesting whether to end the currently selected exercise. For example, the visual object 1310 may include a phrase such as "Do you want to end exercise?" or "Do you want to end running?". The processor 120 may receive an input for requesting the end of the exercise plan. For example, when a user input is received via an object corresponding to "yes" among objects included in the visual object 1310, the processor 120 may identify that the currently displayed exercise plan is to be ended.

In operation 1220, the processor 120 may obtain information on a first body temperature of a user wearing a wearable device (e.g., an electronic device 101) via at least one sensor. For example, the processor 120 may identify a first body temperature of a user corresponding to an input time point of the user touch based on a user touch input on an object corresponding to "Yes" in the visual object 1310 of FIG. 13A.

In operation 1230, the processor 120 may determine whether the first body temperature is less than the first reference temperature. The first reference temperature may be a temperature for determining whether the user needs to perform a cool-down exercise. For example, when the first body temperature is lower than the first reference temperature, the processor 120 may determine that the first body temperature is lower than the first reference temperature because the user has performed a separate cool-down exercise, or has already ended the exercise and taken a rest. The processor 120 may display a screen for displaying an exercise result immediately without guiding a cool-down exercise.

In operation 1240, the processor 120 may display a second screen for guiding a cool-down exercise distinguished from the first screen displayed in response to the end of the exercise plan. For example, referring to FIG. 13B together, the display 700 may display a first screen. The first screen may include a visual object 1320 indicating an exercise result. For example, when the exercise plan performed by the user is a run, the visual object 1320 may include objects indicating a start and end time of the run, a total exercise time, calories consumed via the run, and/or an average running speed.

According to various embodiments, the processor 120 may bypass displaying the first screen and display a second screen different from the first screen. The second screen may be a screen for guiding a cool-down exercise. For example, when the first body temperature is higher than or equal to the first reference temperature, in order to guide the cool-down exercise, the processor 120 may display a second screen for guiding a cool-down exercise, instead of displaying a visual object 1320 indicating the outcome of the run. For example, referring to FIG. 13C together, the processor 120 may display a visual notification for a cool-down exercise. The processor 120 may display a visual object 1330 including a phrase indicating the start of a cool-down exercise via the display 700. For example, the visual object 1330 may include a phrase of "starting a cool-down exercise."

In operation 1250, the processor 120 may obtain information on the second body temperature of the user wearing the wearable device via at least one sensor. The second body temperature may correspond to the user's body temperature being measured while the second screen is displayed via the display 220. For example, referring to FIG. 8C together, a visual object guiding the posture and/or the number of times of a cool-down exercise may be displayed via the second screen. The user may perform a cool-down exercise based on the guide of the second screen. As the user performs a cool-down exercise, the body temperature may decrease.

In operation 1260, the processor 120 may identify whether the second body temperature reaches the second reference temperature. The second reference temperature may be a temperature that determines end of the cool-down exercise. For example, the second reference temperature may be a temperature lower than the first reference temperature.

In an embodiment, the second reference temperature may be fixedly set to a designated temperature value. For example, the second reference temperature may be a fixed value of about 37° C. The processor 120 may end the cool-down exercise in response to identifying that the second body temperature reaches about 37° C., which is the second reference temperature. In another embodiment, the second reference temperature may be variably set. The second reference temperature may be determined based on the first body temperature. For example, when the first body temperature is high (e.g., 38° C.), the second reference temperature for ending cool-down exercise may be set to be lower in order to increase resilience after exercise. For example, the second reference temperature may be set to a temperature 1° C. lower than the first body temperature in order to induce sufficient cool-down exercise. As another example, when the first body temperature is low (e.g., 36° C.), the second reference temperature for ending the cool-down exercise may be set to be higher because the resilience after exercise is relatively better than when the first body temperature is high. For example, the second reference temperature may be set to a temperature 0.5° C. lower than the first body temperature. According to an embodiment, the second reference temperature may be a variable set based on the intensity of the exercise plan requested to end. For example, when the exercise plan is running and the exercise distance is 30 Km, a sufficient cool-down exercise may be required for rapid recovery since there are more fatigue substances than when the exercise distance is 5 Km. Accordingly, the processor 120 may induce sufficient cool-down exercise by setting the second reference temperature to be lower.

In another embodiment, the second reference temperature may be determined based on an external temperature of the electronic device 101. According to various embodiments, the processor 120 may obtain information on an external environment of the electronic device 101 via the sensor module 176. For example, the processor 120 may obtain information on an external temperature and an external humidity of the electronic device 101 via a temperature sensor and a humidity sensor included in the sensor module 176. For example, when the external temperature is cold weather of 10° C. or less, the second reference temperature may be set to a temperature higher than 1° C. from the first body temperature. For another example, when the external temperature is warm weather of 30° C. or more, the second reference temperature may be set to a temperature higher than 0.5° C. from the first body temperature.

In operation 1270, the processor 120 may switch the second screen to the first screen. When the body temperature rises to reach the second reference temperature as performing the warm-up exercise shown in FIG. 8C, the processor 120 may identify that the user has performed a cool-down exercise. The processor 120 may change the second screen displayed via the display 220 to the first screen. The processor 120 may display a screen corresponding to an input requesting the end of the exercise plan received in operation 1210. For example, the processor 120 may display a first screen indicating a result of a running exercise. For example, the first screen may include the visual object 1320 of FIG. 13B.

Figure 14:
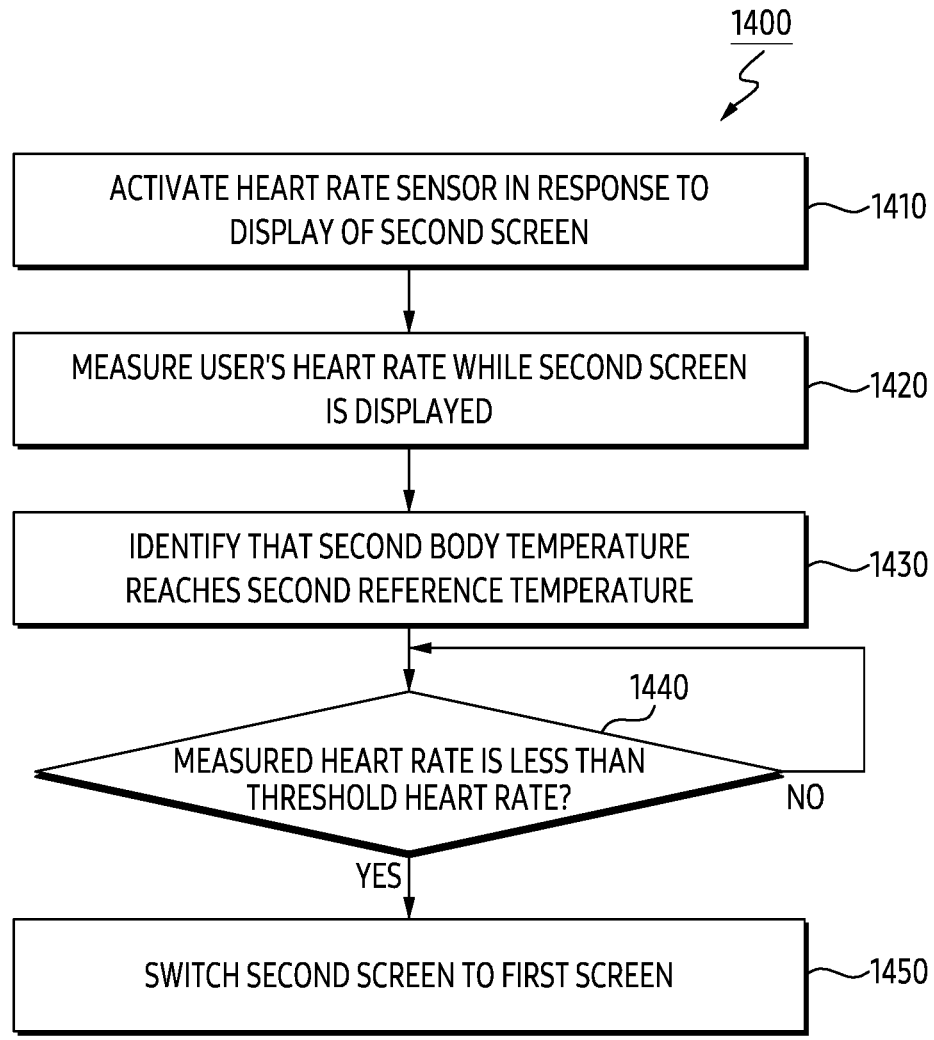
FIG. 14 is a flowchart illustrating an operation of an electronic device for guiding a cooling-down exercise according to various embodiments.

FIG. 14 is a flowchart illustrating an operation of an electronic device 101 for guiding a cooling-down exercise according to various embodiments.

Referring to FIG. 14, in operation 1410, the processor 120 may activate the heart rate sensor in response to the display of the second screen. The heart rate sensor is a sensor for measuring a user's heart rate, and may correspond to at least one of the PPG sensor 520 and the bio electrode sensor 540 of FIG. 5A.

In operation 1420, the processor 120 may measure the user's heart rate while the second screen is displayed. As the user performs a cool-down exercise guided through the second screen, the measured heart rate while the second screen is displayed may be reduced.

In operation 1430, the processor 120 may identify that the second body temperature reaches the second reference temperature. Operation 1430 may correspond to operation 1260 of FIG. 12.

In operation 1440, processor 120 may identify whether the measured heart rate is less than the threshold heart rate. The threshold heart rate may be a value for determining whether to end the second screen for guiding a cool-down exercise. For example, when the user has sufficiently performed a cool-down exercise according to the second screen, the measured heart rate may be lower than the threshold heart rate.

According to an embodiment, when the measured heart rate in operation 1440 exceeds the threshold heart rate, the processor 120 may continuously monitor the user's heart rate based on the heart rate sensor.

According to another embodiment, when the heart rate measured in operation 1440 is less than the threshold heart rate, the processor 120 may perform operation 1450 to switch the second screen to the first screen. That is, the processor 120 may identify that the second body temperature reaches the second reference temperature by sufficiently performing a cool-down exercise by the user, and may identify that the heart rate got lower than the threshold heart rate substantially simultaneously. That is, the processor 120 may determine whether sufficient cool-down exercise had been performed after the main exercise (e.g., running) based on both the body temperature and the heart rate.

In the above-described embodiment, the processor 120 is described as determining whether the heart rate measured after the operation 1430 of identifying that the second body temperature reaches the second reference temperature exceeds the threshold heart rate, but is not limited thereto. The processor 120 may measure the body temperature and the heart rate substantially simultaneously and determine whether conditions for ending the second screen are achieved, respectively. For example, the processor 120 may substantially simultaneously and in parallel determine whether the second body temperature reaches the second reference temperature and whether the measured heart rate is less than the threshold heart rate.

Figure 15:
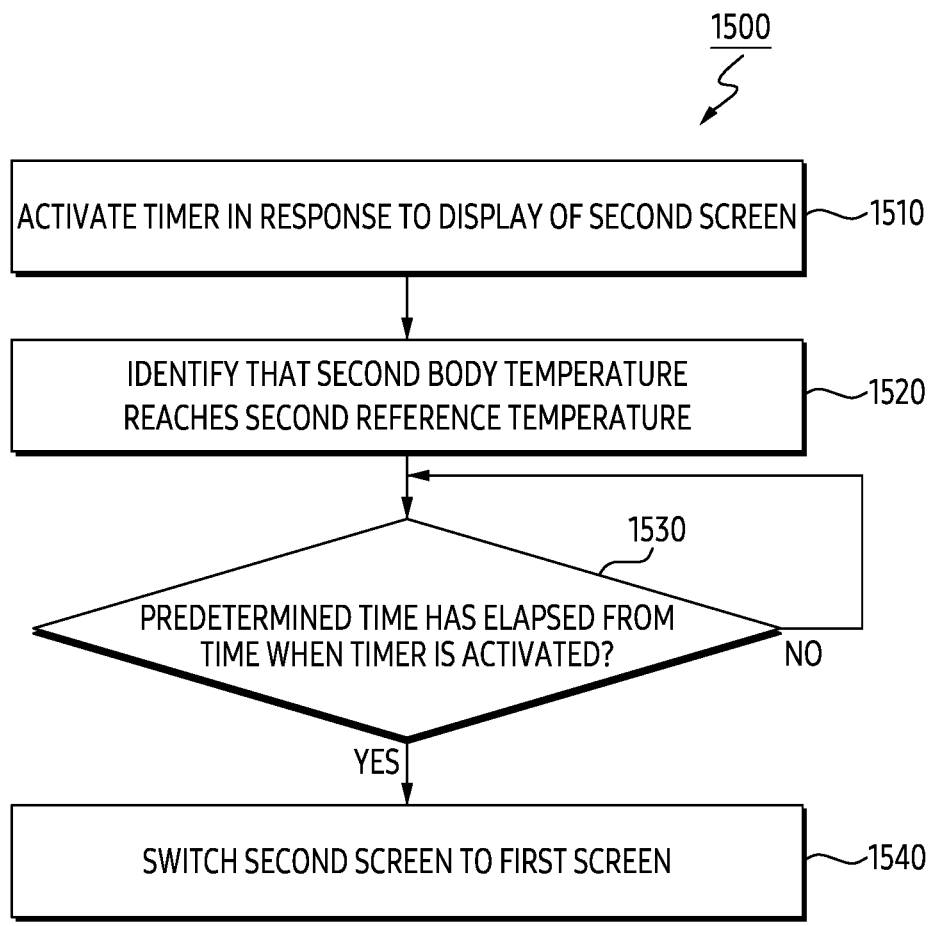
FIG. 15 is a flowchart illustrating an operation of an electronic device for guiding a cooling-down exercise according to various embodiments.

FIG. 15 is a flowchart illustrating an operation of an electronic device 101 for guiding a cooling-down exercise according to various embodiments.

Referring to FIG. 15, in operation 1510, the processor 120 may activate the timer in response to the display of the second screen. The timer may be for determining whether a predetermined time elapses from a time point at which the second screen is displayed.

According to an embodiment, the predetermined time may have a fixed length. For example, the predetermined time may be set to 5 minutes. In this case, the processor 120 may display the second screen for at least 5 minutes.

According to another embodiment, the predetermined time may have a variable length. The predetermined time may be variably set based on an external temperature of the electronic device 101. For example, when the external temperature is cold weather of 10° C. or less, the predetermined time may be set briefly to 5 minutes. For another example, when the external temperature is warm weather of 30° C. or more, the predetermined time may be set longer to 10 minutes. For example, when the external humidity is high, the predetermined time may be briefly set to 5 minutes. According to an embodiment, the predetermined time may be set variable based on the intensity of the exercise plan requested to end. For example, when the exercise plan is running and the exercise distance is 30 Km, more fatigue substances are generated than when the exercise distance is 5 Km, and thus sufficient cool-down exercise may be required for fast recovery. Accordingly, the processor 120 may induce sufficient cool-down exercise by setting the predetermined length of time to be longer.

In operation 1520, the processor 120 may identify that the second body temperature reaches the second reference temperature. Operation 1530 may correspond to operation 1260 of FIG. 12.

In operation 1530, the processor 120 may identify whether a predetermined time has elapsed from the time when the timer is activated. When a predetermined time has not elapsed from the time point when the second screen is displayed, the processor 120 may continuously display the second screen. For example, when the predetermined time has not elapsed, the second screen may be continuously displayed through the display 220 even when the second body temperature reaches the second reference temperature. For another example, when the predetermined time has elapsed, the processor 120 may switch the second screen to the first screen in operation 1540. Operation 1540 may correspond to operation 1270 of FIG. 12.

In the above-described embodiment, the processor 120 is described as determining whether a predetermined time elapses from the time point at which the timer is activated after the operation 1520 identifying that the second body temperature reaches the second reference temperature, but is not limited thereto. The processor 120 may identify that the predetermined time has elapsed before the second body temperature reaches the second reference temperature. When the second body temperature does not reach the second reference temperature even after a predetermined time has elapsed, the processor 120 may display the second screen until the second body temperature reaches the second reference temperature.

According to various embodiments, a wearable device (e.g., the electronic device 101 of FIG. 1) may comprise at least one memory (e.g., the memory 130 of FIG. 1) configured to store instructions, at least one processor (e.g., the processor 120 of FIG. 1), at least one sensor (e.g., the sensor module 176 of FIG. 1), and a display (e.g., the display 220 of FIG. 3); wherein when the instructions are executed, the at least one processor is configured to receive, via the display, an input with respect to an item among a plurality of items respectively representing an exercise plan; in response to the receiving of the input, obtain, via the at least one sensor, information for a first body temperature of a user wearing the wearable device; in response to identify that the first body temperature is less than a first reference temperature, display a second screen guiding a warm-up exercise distinguishable from a first screen guiding an exercise plan indicated by the item corresponding to the input; obtain, via the at least one sensor, a second body temperature of the user, while the second screen is displayed; and in response to identify that the second body temperature reaches to a second reference temperature, switch the second screen to the first screen.

According to an embodiment, the at least one sensor may include at least one of a body temperature sensor for measuring a body temperature of the user, a heart rate sensor for measuring a heart rate of the user, and a 6-axis sensor for measuring a movement of the wearable device.

According to an embodiment, the at least one processor may, when the instructions are executed, be configured to display, based on identifying that the first body temperature is less than the first reference temperature, a visual object for notifying that the second screen guiding the warm-up exercise is displayed.

According to an embodiment, the at least one processor may, when the instructions are executed, be configured to identify, in response to displaying the second screen, via the at least one sensor, a movement of the wearable device, and identify, via the at least one sensor, a heart rate of the user.

According to an embodiment, the at least one processor may, when the instructions are executed, be configured to acquire, via the at least one sensor, a peripheral information for an external environment of the wearable device, and set the second reference temperature variably, based on the peripheral information and the item from among the plurality of items.

According to an embodiment, the peripheral information may include at least one of an external temperature of the wearable device and an external humidity of the wearable device, and wherein the at least one processor may be configured to set the second reference temperature variably to be inversely proportional to the external temperature, and set the second reference temperature variably to be proportional to an intensity of an exercise identified based on the item from among the plurality of items.

According to an embodiment, the at least one processor may, when the instructions are executed, be configured to identify that a predefined time is passed from a time displaying the second screen, in response to identifying that the second body temperature reaches to the second reference temperature, and switch the second screen to the first screen in response to identifying that the predefined time is passed.

According to an embodiment, the peripheral information may include at least one of an external temperature of the wearable device and an external humidity of the wearable device which are acquired by the at least one sensor, and wherein the at least one processor may be configured to set a duration of the predefined time variably to be inversely proportional to the external humidity and the external temperature.

According to an embodiment, the at least one processor may, when the instructions are executed, be configured to identify that a size of the identified movement or magnitude of the identified heart rate is less than a threshold value, and in response to the identification, display, via the display, a visual object to check whether the second screen guiding the warm-up exercise switches to the first screen.

According to an embodiment, the at least one processor may, when the instructions are executed, be configured to perform monitoring for the heart rate of the user, via the at least one sensor, in response to displaying the second screen guiding the warm-up exercise, identify that magnitude of the monitored heart rate exceeds a predetermined value, in response to identifying that the second body temperature reaches the second reference temperature and switch the second screen to the first screen, in response to the identification.

According to various embodiments, a wearable device (e.g., the electronic device 101 of FIG. 1) may include at least one memory (e.g., the memory 130 of FIG. 1) configured to store instructions, at least one processor (e.g., processor 120 in FIG. 1), at least one sensor (e.g., sensor module 176 in FIG. 1), and a display (e.g., display 220 in FIG. 3); wherein when the instructions are executed, the at least one processor may be configured to receive an input requesting an end of an exercise plan displayed via the display; in response to receiving of the input, acquire, via the at least one sensor, information for a first body temperature of a user wearing the wearable device, in response to identify that the first body temperature exceeds a first reference temperature, display a second screen guiding a cool-down exercise distinguishable from a first screen displayed responsive to the end of the exercise plan; acquire, via the at least one sensor, a second body temperature of the user, while the second screen is displayed; and in response to identify that the second body temperature reaches to a second reference temperature lower than the first reference temperature, switch the second screen to the first screen.

According to an embodiment, the at least one sensor may include at least one of a body temperature sensor for measuring a body temperature of the user, a heart rate sensor for measuring a heart rate of the user, and a 6-axis sensor for measuring a movement of the wearable device.

According to an embodiment, the at least one processor may, when the instructions are executed, be configured to display a visual object for notifying that the second screen guiding the cool-down exercise is displayed in response to identifying that the first body temperature exceeds the first reference temperature.

According to an embodiment, the at least one processor may, when the instructions are executed, be configured to identify, via the at least one sensor, a movement of the wearable device in response to displaying the second screen; and identify, via the at least one sensor, a heart rate of the user.

According to an embodiment, the at least one processor may, when the instructions are executed, be configured to acquire, via the at least one sensor, a peripheral information for an external environment of the wearable device; and set the second reference temperature variably, based on the peripheral information and the exercise plan.

According to an embodiment, the peripheral information may include at least one of an external temperature of the wearable device and an external humidity of the wearable device; and wherein the at least one processor may be configured to set the second reference temperature variably based on the external temperature and an exercise intensity of the exercise plan.

According to an embodiment, the at least one processor may, when the instructions are executed, be configured to identify that a predefined time is passed from a time displaying the second screen in response to identifying that the second body temperature reaches to the second reference temperature, and switch the second screen to the first screen in response to identifying that the predefined time is passed.

According to an embodiment, the peripheral information may include at least one of an external temperature of the wearable device and an external humidity of the wearable device which are acquired by the at least one sensor, and the at least one processor may be configured to set a duration of the predefined time variably to the external humidity and the external temperature.

According to an embodiment, the at least one processor may, when the instructions are executed, be configured to identify that a size of the identified movement or magnitude of the identified heart rate is less than a threshold value, and in response to the identification, display, via the display, a visual object to check whether the second screen guiding the cool-down exercise switches to the first screen.

According to an embodiment, the at least one processor may, when the instructions are executed, be configured to perform monitoring for the heart rate of the user, via the at least one sensor, in response to displaying the second screen guiding the cool-down exercise; identify that a magnitude of the monitored heart rate is less than a predetermined value, in response to identifying that the second body temperature reaches the second reference temperature, and switch the second screen to the first screen in response to the identification.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "$1^{st}$" and "$2^{nd}$," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to.". "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may be interchangeably used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

What is claimed is:

1. A wearable device, comprising:
   at least one memory configured to store a plurality of instructions;
   at least one processor;
   at least one sensor; and
   a display that is touch-sensitive,
   wherein when the instructions are executed, the at least one processor is configured to:
   receive, via the display, an input with respect to an item among a plurality of items respectively representing an exercise plan,
   in response to the receiving of the input, acquire, via the at least one sensor, information for a first body temperature of a user wearing the wearable device,
   in response to identifying that the first body temperature is less than a first reference temperature, display a second screen guiding a warm-up exercise distinguishable from a first screen guiding the exercise plan indicated by the item corresponding to the input,
   acquire, via the at least one sensor, a second body temperature of the user, while the second screen is displayed, and
   in response to identifying that the second body temperature reaches to a second reference temperature, switch the second screen to the first screen.

2. The wearable device of claim 1, wherein the at least one sensor includes at least one of a body temperature sensor for measuring a body temperature of the user, a heart rate sensor for measuring a heart rate of the user, and a 6-axis sensor for measuring a movement of the wearable device.

3. The wearable device of claim 1, wherein when the instructions are executed, the at least one processor is configured to:
   based on identifying that the first body temperature is less than the first reference temperature, display a visual object for notifying that the second screen guiding the warm-up exercise is displayed.

4. The wearable device of claim 1, wherein when the instructions are executed, the at least one processor is configured to:
   in response to displaying the second screen, identify, via the at least one sensor, a movement of the wearable device, and
   identify, via the at least one sensor, a heart rate of the user.

5. The wearable device of claim 1, wherein when the instructions are executed, the at least one processor is configured to:
   acquire, via the at least one sensor, peripheral information for an external environment of the wearable device, and
   set the second reference temperature variably, based on the peripheral information and the item from among the plurality of items.

6. The wearable device of claim 5, wherein the peripheral information includes at least one of an external temperature of the wearable device and an external humidity of the wearable device, and
   wherein the at least one processor is configured to:
   set the second reference temperature variably to be inversely proportional to the external temperature, and
   set the second reference temperature variably to be proportional to an intensity of an exercise identified based on the item from among the plurality of items.

7. The wearable device of claim 5, wherein when the instructions are executed, the at least one processor is configured to:
   in response to identifying that the second body temperature reaches to the second reference temperature, identify that a predefined time is passed from a time displaying the second screen, and
   in response to identifying that the predefined time is passed, switch the second screen to the first screen.

8. The wearable device of claim 7, wherein the peripheral information includes at least one of an external temperature of the wearable device and an external humidity of the wearable device which are acquired by the at least one sensor, and
   wherein the at least one processor is configured to set a duration of the predefined time variably to be inversely proportional to the external humidity and the external temperature.

9. The wearable device of claim 4, wherein when the instructions are executed, the at least one processor is configured to:
   identify that a size of the identified movement of the wearable device or a magnitude of the identified heart rate of the user is less than a threshold value, and
   in response to the identification, display, via the display, a visual object to check whether the second screen guiding the warm-up exercise switches to the first screen.

10. The wearable device of claim 1, wherein when the instructions are executed, the at least one processor is configured to:
    in response to displaying the second screen guiding the warm-up exercise, perform monitoring for a heart rate of the user, via the at least one sensor,
    in response to identifying that the second body temperature reaches the second reference temperature, identify that a magnitude of the monitored heart rate exceeds a predetermined value, and
    in response to the identification, switch the second screen to the first screen.

11. A wearable device, comprising:
    at least one memory configured to store instructions;
    at least one processor;
    at least one sensor; and
    a display,
    wherein when the instructions are executed, the at least one processor is configured to:
    receive an input requesting an end of an exercise plan displayed via the display,
    in response to receiving of the input, acquire, via the at least one sensor, information for a first body temperature of a user wearing the wearable device,
    in response to identifying that the first body temperature exceeds a first reference temperature, display a second screen guiding a cool-down exercise distinguishable from a first screen displayed responsive to the end of the exercise plan, acquire, via the at least one sensor, a second body temperature of the user, while the second screen is displayed, and in response to identifying that the second body temperature reaches to a second reference temperature lower than the first reference temperature, switch the second screen to the first screen.

12. The wearable device of claim 11, wherein the at least one sensor includes at least one of a body temperature sensor for measuring a body temperature of the user, a heart rate sensor for measuring a heart rate of the user, and a 6-axis sensor for measuring a movement of the wearable device.

13. The wearable device of claim 11, wherein when the instructions are executed, the at least one processor is configured to:

in response to identifying that the first body temperature exceeds the first reference temperature, display a visual object for notifying that the second screen guiding the cool-down exercise is displayed.

14. The wearable device of claim 11, wherein when the instructions are executed, the at least one processor is configured to:

in response to displaying the second screen, identify, via the at least one sensor, a movement of the wearable device, and identify, via the at least one sensor, a heart rate of the user.

15. The wearable device of claim 11, wherein when the instructions are executed, the at least one processor is configured to:

acquire, via the at least one sensor, peripheral information for an external environment of the wearable device, and set the second reference temperature variably, based on the peripheral information and the exercise plan.

16. The wearable device of claim 15, wherein the peripheral information includes at least one of an external temperature of the wearable device and an external humidity of the wearable device, and wherein the at least one processor is configured to:

set the second reference temperature variably based on the external temperature and an exercise intensity of the exercise plan.

17. The wearable device of claim 15, wherein when the instructions are executed, the at least one processor is configured to:

in response to identifying that the second body temperature reaches to the second reference temperature, identify that a predefined time is passed from a time displaying the second screen, and in response to identifying that the predefined time is passed, switch the second screen to the first screen.

18. The wearable device of claim 17, wherein the peripheral information includes at least one of an external temperature of the wearable device and an external humidity of the wearable device which are acquired by the at least one sensor, and wherein the at least one processor is configured to set a duration of the predefined time variably to the external humidity and the external temperature.

19. The wearable device of claim 14, wherein when the instructions are executed, the at least one processor is configured to:

identify that a size of the identified movement of the wearable device or a magnitude of the identified heart rate of the user is less than a threshold value, and in response to the identification, display, via the display, a visual object to check whether the second screen guiding the cool-down exercise switches to the first screen.

20. The wearable device of claim 11, wherein when the instructions are executed, the at least one processor is configured to:

in response to displaying the second screen guiding the cool-down exercise, perform monitoring for a heart rate of the user, via the at least one sensor, in response to identifying that the second body temperature reaches the second reference temperature, identify that a magnitude of the monitored heart rate is less than a predetermined value, and in response to the identification, switch the second screen to the first screen.

* * * * *